United States Patent [19]

Payne et al.

[11] Patent Number: 5,668,148

[45] Date of Patent: Sep. 16, 1997

[54] ALPHA1A ADRENERGIC RECEPTOR ANTAGONISTS

[75] Inventors: Linda S. Payne; Steven D. Young, both of Lansdale, Pa.; Mary Jo L. Zaborowski, Westfield, N.J.

[73] Assignee: Merck & Co., Inc., Rahway, N.J.

[21] Appl. No.: 425,969

[22] Filed: Apr. 20, 1995

[51] Int. Cl.$^6$ .......... A61K 31/47; A61K 31/415; A61K 31/42; A61K 31/425; A61K 31/445; C07D 401/04; C07D 409/04

[52] U.S. Cl. .......... 514/314; 514/307; 514/318; 514/321; 514/322; 514/323; 514/324; 514/326; 514/367; 514/372; 514/373; 514/375; 514/378; 514/379; 514/394; 514/406; 546/139; 546/167; 546/193; 546/194; 546/196; 546/197; 546/198; 546/199; 546/201; 546/202; 546/205; 546/211; 548/152; 548/159; 548/206; 548/207; 548/217; 548/241; 548/247; 548/306.1; 548/361.1; 548/364.1; 548/364.4; 548/365.7

[58] Field of Search .................. 546/167, 194, 546/197, 211, 139, 193, 196, 198, 199, 201, 202, 205; 574/314, 318, 321, 326, 307, 322, 323, 324, 367, 372, 373, 375, 378, 379, 394, 406; 548/152, 159, 207, 217, 241, 306.1, 361, 364.1, 364.4, 365.7, 206, 247

[56] References Cited

U.S. PATENT DOCUMENTS 5,403,847  4/1995  Gluchowski et al. .......... 514/318

FOREIGN PATENT DOCUMENTS

| | | |
|---|---|---|
| 0 135 781 | 4/1985 | European Pat. Off. . |
| 0 296 721 A3 | 12/1988 | European Pat. Off. . |
| 0 316 718 24 | 5/1989 | European Pat. Off. . |
| 0 402 644 A1 | 12/1990 | European Pat. Off. . |
| 94/08040 | 4/1994 | WIPO . |
| 94/10145 | 5/1994 | WIPO . |
| 94/10162 | 5/1994 | WIPO . |
| 94/10989 | 5/1994 | WIPO . |
| 94/21660 | 9/1994 | WIPO . |

OTHER PUBLICATIONS

Metcalf BW, Levy MA, Holt DA, TIPS 10, pp. 490–495. Dec. 1989.

*Primary Examiner*—C. Warren Ivy
*Assistant Examiner*—Evelyn Huang
*Attorney, Agent, or Firm*—Mary A. Appollina; Melvin Winokur

[57] ABSTRACT

Compounds that specifically bind to the human alpha1a adrenergic receptor, including compounds effective to reduce symptoms of benign prostatic hypertrophy include compounds of formula:

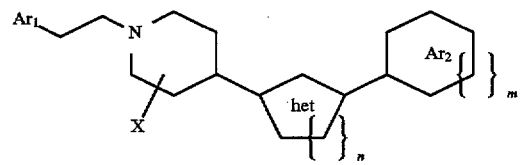

wherein:
Ar1 and Ar2 can be independantly aromatic, heteroaromatic, or condensed heteroaromatic unsubstituted or substituted with amino, alkoxy, sulfonamido, alkyl, heteroalkyl, halo;

m is 0 or 1;

n is 0, 1, or 2;

het is an aromatic or nonaromatic heterocyclic ring, substituted with alkyl, halo, or alkoxy substituents; and X is a branched or straight chain aliphatic or halogen substituent.

12 Claims, No Drawings

ALPHA1A ADRENERGIC RECEPTOR ANTAGONISTS

FIELD OF THE INVENTION

This invention relates to certain novel compounds and derivatives thereof, their synthesis, and their use as selective alpha-1a adrenoceptor antagonists. More particularly, the compounds of the present invention are useful for treating benign pro static hypertophy (BPH).

BACKGROUND OF THE INVENTION

Human adrenergic receptors are integral membrane proteins which have been classified into two broad classes, the alpha and the beta adrenergic receptors. Both types mediate the action of the peripheral sympathetic nervous system upon binding of catecholamines, norepinephrine and epinephrine.

Norepinephrine is produced by adrenergic nerve endings, while epinephrine is produced by the adrenal medulla. The binding affinity of adrenergic receptors for these compounds forms one basis of the classification: alpha receptors bind norepinephrine more strongly than epinephrine and much more strongly than the synthetic compound isoproterenol. The binding affinity of these hormones is reversed for the beta receptors. In many tissues, the functional responses, such as smooth muscle contraction, induced by alpha receptor activation are opposed to responses induced by beta receptor binding.

Subsequently, the functional distinction between alpha and beta receptors was further highlighted and refined by the pharmacological characterization of these receptors from various animal and tissue sources. As a result, alpha and beta adrenergic receptors were further subdivided into $\alpha_1$, $\alpha_2$, $\beta_1$, and $\beta_2$ subtypes. Functional differences between $\alpha_1$ and $\alpha_2$ receptors have been recognized, and compounds which exhibit selective binding between these two subtypes have been developed. Thus, in WO 92/0073, the selective ability of the R(+) enantiomer of terazosin to selectively bind to adrenergic receptors of the alpha 1 subtype was reported. The $\alpha_1/\alpha_2$ selectivity of this compound was disclosed as being significant because agonist stimulation of the $\alpha_2$ receptors was said to inhibit secretion of epinephrine and norepinephrine, while antagonism of the $\alpha_2$ receptor was said to increase secretion of these hormones. Thus, the use of non-selective alpha-adrenergic blockers, such as phenoxybenzamine and phentolamine, is limited by their $\alpha_2$ adrenergic receptor mediated induction of increased plasma catecholamine concentration and the attendant physiological sequelae (increased heart rate and smooth muscle contraction).

For a general background on the $\alpha$-adrenergic receptors, the reader's attention is directed to Robert R. Ruffolo, Jr., α-*Adrenoreceptor: Molecular Biology, Biochemistry and Pharmacology*, (*Progress in Basic and Clinical Pharmacology* series, Karger, 1991), wherein the basis of $\alpha_1/\alpha_2$ subclassification, the molecular biology, signal transduction (G-protein interaction and location of the significant site for this and ligand binding activity away from the 3'-terminus of alpha adrenergic receptors), agonist structure-activity relationships, receptor functions, and therapeutic applications for compounds exhibiting $\alpha$-adrenergic receptor affinity was explored.

The cloning, sequencing and expression of alpha receptor subtypes from animal tissues has led to the subclassification of the $\alpha_1$ receptors into $\alpha_{1a}$, (Lomasney, et al., *J. Biol. Chem.*, 266:6365–6369 (1991), rat $\alpha_{1a}$; Bruno et al., *BBRC*, 179:1485–1490 (1991), human $\alpha_{1a}$), $\alpha_{1b}$ (Cotecchia, et al., *PNAS*, 85;7159–7163 (1988), hamster $\alpha_{1b}$; Libert, et al., *Science*, (1989), dog $\alpha_{1b}$; Ramarao, et al., *J. Biol. Chem.*, 267:21936–21945 (1992), human $\alpha_{1b}$), and most recently, in a study using bovine brain, a new $\alpha_{1c}$ subtype was proposed (Schwinn, et al., *J. Biol. Chem.*, 265:8183–8189 (1990); Hirasawa et al., *BBRC* 195:902–909 (1993), described the cloning, functional expression and tissue distribution of a human $\alpha_{1c}$ adrenergic receptor; Hoehe et al., *Human Mol. Genetics* 1(5):349 (8/92) noted the existence of a two-allele Pst1 restriction fragment polymorphism in the $\alpha_{1c}$ adrenergic receptor gene; another study suggests that there may even be an alpha-1d receptor subtype, see Perez et al., *Mol. Pharm.*, 40:876–883, 1992). Each $\alpha_1$ receptor subtype exhibits its own pharmacologic and tissue specificities. Schwinn and coworkers noted that the cloned bovine $\alpha_{1c}$ receptor exhibited pharmacological properties proposed for the $\alpha_{1a}$ subtype. Nonetheless, based on its non-expression in tissues where the $\alpha_{1a}$ subtype is expressed, and its sensitivity to chloroethylclonidine, the receptor was given a new designation.

The differences in the $\alpha$-adrenergic receptor subtypes have relevance in pathophysiologic conditions. Benign prostatic hypertrophy, also known as benign prostatic hyperplasia or BPH, is an illness typically affecting men over fifty years of age, increasing in severity with increasing age. The symptoms of the condition include, but are not limited to, increased difficulty in urination and sexual dysfunction. These symptoms are induced by enlargement, or hypertrophy, of the prostate gland. As the prostate increases in size, it impinges on free-flow of fluids through the male urethra. Concommitantly, the increased noradrenergic innervation of the enlarged prostate leads to an increased adrenergic tone of the bladder neck and urethra, further restricting the flow of urine through the urethra.

In benign prostatic hypertrophy, the male hormone 5α-dihydrotestosterone has been identified as the principal culprit. The continual production of 5α-dihydrotestosterone by the male testes induces incremental growth of the prostate gland throughout the life of the male. Beyond the age of about fifty years, in many men, this enlarged gland begins to obstruct the urethra with the pathologic symptoms noted above.

The elucidation of the mechanism summarized above has resulted in the recent development of effective agents to control, and in many cases reverse, the pernicious advance of BPH. In the forefront of these agents is Merck & Co., Inc.s' product PROSCAR® (finasteride). The effect of this compound is to inhibit the enzyme testosterone 5-alpha reductase, which converts testosterone into 5α-dihydrotesterone, resulting in a reduced rate of prostatic enlargement, and often reduction in prostatic mass.

The development of such agents as PROSCAR® bodes well for the long-term control of BPH. However, as may be appreciated from the lengthy development of the syndrome, its reversal also is not immediate. In the interim, those males suffering with BPH continue to suffer, and may in fact lose hope that the agents are working sufficiently rapidly.

In response to this problem, one solution is to identify pharmaceutically active compounds which complement slower-acting therapeutics by providing acute relief. Agents which induce relaxation of the urethral smooth muscle, by binding to alpha-1 adrenergic receptors, thus reducing the increased adrenergic tone due to the disease, would be good candidates for this activity. Thus, one such agent is alfuzosin, which is reported in EP 0 204597 to induce urination in cases of prostatic hypertrophy. Likewise, as mentioned above, it has been reported that the R(+) enantiomer of terazosin selectively binds to adrenergic receptors of the alpha 1 subtype. In addition, in WO 92/161213, hereby incorporated by reference, combinations of 5-alpha-reductase inhibitory compounds and alpha1-adrenergic receptor blockers (terazosin, doxazosin, prazosin, bunazosin, indoramin, alfuzosin) were disclosed. However, no information as to the $\alpha_{1a}$, $\alpha_{1b}$, or $\alpha_{1c}$ subtype specificity of these compounds was provided as this data and its relevancy to the treatment of BPH was not known. Current therapy for BPH uses existing non-selective alpha-1 antagonists such as prazosin (Minipress, Pfizer), Terazosin (Hytrin, Abbott) or doxazosin mesylate (Cardura, Pfizer). These non-selective antagonists suffer from side effects related to antagonism of the alpha-1a and alpha-1b receptors in the peripheral vasculature, e.g., orthostatic hypotension and syncope.

Typically, identification of active compounds is accomplished through use of animal tissues known to be enriched in adrenergic receptors. Thus, rat tissues have been used to screen for potential adrenergic receptor antagonists. However, because of species variability, compounds which appear active in animal tissue may not be active or sufficiently selective in humans. This results in substantial wastage of time and effort, particularly where high volume compound screening programs are employed. There is also the danger that compounds, which might be highly effective in humans, would be missed because of their absence of appreciable affinity for the heterologous animal receptors. In this regard, it has been noted that even single amino acid changes between the sequence of biologically active proteins in one species may give rise to substantial pharmacological differences. Thus, Fong et al., (*J. Biol. Chem.* 267:25668–25671, 1992) showed that there are 22 divergent amino acid residues between the sequence of the human neurokinin-1 receptor and the homologous rat receptor. They further showed, in studies with mutant receptors, that substitution of only two amino acid residues was both necessary and sufficient to reproduce the rat receptor's antagonist binding affinity in the human receptor. Oksenberg et al., (*Nature*, 360:161–163, 1992) showed that a single amino-acid difference confers major pharmacological variation between the human and the rodent 5-hydroxytryptamine receptors. Likewise, Kuhse et al., (*Neuron*, 5:867–873, 1990) showed that a single amino-acid exchange alters the pharmacology of the neonatal rat glycine receptor subunit. This difficulty and unpredictability has resulted in a need for a compound screen which will identify compounds that will be active in humans.

These problems were solved by cloning the human adrenergic receptor of the $\alpha_{1c}$ subtype (ATCC CRL 11140) and the use of a screening assay which enables identification of compounds which specifically interact with the human α1c adrenergic receptor. [PCT International Application Publication Nos. WO94/08040, published 14 Apr. 1994 and WO94/10989, published 26 May 1994]. As disclosed in the instant patent disclosure, a cloned human $\alpha_{1c}$ adrenergic receptor and a method for identifying compounds which bind the human $\alpha_{1c}$ receptor has now made possible the identification of selective human $\alpha_{1c}$ adrenergic receptor antagonists useful for treating BPH. The instant patent disclosure discloses novel compounds which selectively bind to the human $\alpha_{1c}$ receptor. These compounds are further tested for binding to other human alpha 1 receptor subtypes, as well as counterscreened against other types of receptors, thus defining the specificity of the compounds of the present invention for the human $\alpha_{1c}$ adrenergic receptor.

Compounds of this invention are used to reduce the acute symptoms of BPH. Thus, compounds of this invention may be used alone or in conjunction with a more long-term anti-BPH therapeutics, such as testosterone 5-alpha reductase inhibitors, including PROSCAR® (finasteride). Aside from their utility as anti-BPH agents, these compounds may be used to induce highly tissue-specific, localized $\alpha_{1c}$ adrenergic receptor blockade whenever this is desired. Effects of this blockade include reduction of intra-ocular pressure, control of cardiac arrhythmias, and possibly a host of alpha-1c receptor mediated central nervous system events.

NOMENCLATURE

Recently, a new α1 adrenergic receptor (α1-AR) classification scheme similar to that proposed by Ford, et al. [α1-*Adrenoceptor Classification: Sharpening Occam's Razor, Trends in Pharm. Sci.* 1994, 15, 167–170] was adopted at the August, 1994 meeting of the International Union of Pharmacology (IUPHAR) in Montreal, Canada. The α1-AR genes formerly known as α1a/d, α1b and α1c were renamed α1d, α1b and α1a, respectively. This new naming system reflects the correspondence between the proteins encoded by the α1a and α1b genes (new IUPHAR nomenclature) and the receptors characterized by traditional pharmacological means as α1A and α1B, respectively, in the literature. Recombinant receptors and receptors characterized pharmacologically in tissues are distinguished by lowercase and uppercase subscripts, respectively.

The above discussion contained in the Background section used the former classification scheme (i.e., α1a/d, α1b and α1c); however, hereinafter, the new classification scheme will be utilized (i.e., αd, α1b and α1a). Thus, what was formerly referred to as the α1c receptor (and α1c receptor antagonists) will hereinafter be referred to utilizing the new nomenclature as the α1a receptor (and α1a receptor antagonists).

SUMMARY OF THE INVENTION

The present invention provides a method of treating a disease which is susceptible to treatment by antagonism of the alpha 1a receptor which comprises administering to a subject in need thereof a therapeutically effective amount of a compound of formula I

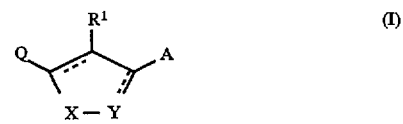

wherein the broken lines represent two non-adjacent double bonds in any position within the five-membered ring, it being understood that bonds to O, S and N—R² are single bonds;

one of X and Y represents nitrogen, and the other of X and Y represents oxygen, sulphur or N—R²;

Q represents a substituted five- or six-membered monocyclic heteroaliphatic ring which contains one nitrogen atom as the sole heteroatom and is linked to the five-membered heteroatomic ring containing the moieties X and Y via a carbon atom;

R¹ represents hydrogen, halogen, $C_{1-6}$ alkyl, hydroxy or $C_{1-6}$ alkoxy;

R² represents hydrogen or $C_{1-6}$ alkyl;

A represents a group of formula (i), (ii), (iii), (iv):

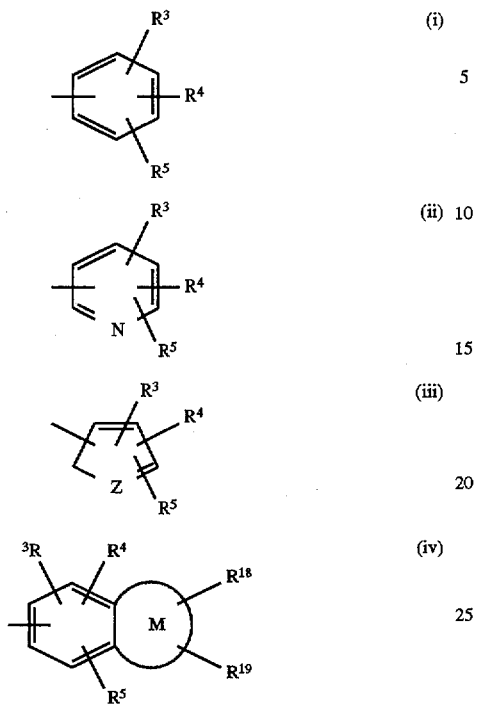

in which Z represents oxygen, sulphur or NH;

$R^3$, $R^4$ and $R^5$ are each independently selected from hydrogen, hydrocarbon, a heterocyclic group, halogen, cyano, trifluoromethyl, nitro, —$OR^a$, —$SR^a$, —$SOR^a$, —$SO_2R^a$, —$SO_2NR^aR^b$, —$NR^aR^b$, —$NR^aCOR^b$, —$NR^aCO_2R^b$, —$COR^a$, —$CO_2R^1$ or —$CO_2NR^aR^b$;

$R^a$ and $R^b$ independently represent hydrogen, hydrocarbon or a heterocyclic group;

the ring M is optionally an additional ring or ring system such that the entire structure (iv) is a monocyclic, dicyclic, or polycyclic aromatic or heteroaromatic ring system, including but not limited to: phenyl; benzodioxane; methylenedioxyphenyl; indane; 2,3,-dihydrobenzofuran; 2,7-dihydroizobenzofuran; 1-naphthyl; 2-naphthyl; benzothiophene; benzofuran; indole; quinoline; isoquinoline; indazole; benzisoxazole; benzthiazole; benzimidazol(on)e; thiophene; furan; pyridine; each of which may be substituted with $R^3$, $R^4$ and $R^5$, as described above and, in addition, with $R^{18}$, and $R^{19}$, each of which may be, independently: $C_{1-6}$ alkyl; $C_{1-6}$ alkoxy-$C_{1-6}$ alkyl; $C_{1-6}$ alkoxy; cyano; nitro; carboxamido; amidino; amino; halo; sulfonamido; amidosulfonyl; hydrogen or hydroxy;

and the pharmaceutically acceptable salts thereof.

In one embodiment of the present invention is a method of treating benign prostatic hypertrophy in a subject in need thereof which comprises administering to the subject a therapeutically effective amount of the compound of formula I described above. In a second embodiment of the present invention is a method of inhibiting contraction of prostate tissue in a subject in need thereof which comprises administering to the subject a therapeutically effective amount of the compound of formula I described above. In preferred embodiments of the present invention, the compound additionally does not cause a fall in blood pressure when administered for treating BPH and inhibiting contraction of prostate tissue.

In a class of the invention are any of the methods described above wherein the five-membered heteroaromatic ring containing the moieties X and Y represented by formula I is a substituted isoxazole, isothiazole or pyrazole ring; and the pharmaceutically acceptable salts thereof.

In a subclass of the invention are any of the methods described above wherein the monocyclic heteroaliphatic ring Q in the compounds of formula I is selected from Qa to Qe:

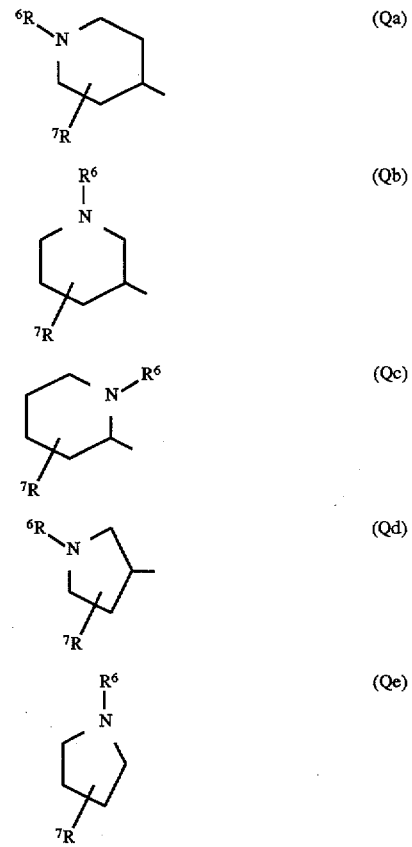

wherein one of $R^6$ and $R^7$ represents hydrocarbon, an ether or a heterocyclic group, and the other of $R^6$ and $R^7$ represents hydrogen, hydrocarbon, an ether or a heterocyclic group;

and the pharmaceutically acceptable salts thereof.

Illustrative of the invention are any of the methods described above wherein $R^6$ is $C_{0-6}$ alkyl substituted with a monocyclic or polycyclic aromatic or heteroaromatic group such as, but are not limited to:

phenyl; 1-naphthyl; 2-naphthyl; benzothiophene; benzofuran; indole; quinoline; isoquinoline; indazole; benzisoxazole; benzimidazol(on)e; thiphene; furan; and pyridine; each of which may or may not be substituted with one or more of $C_{1-6}$ alkyl; $C_{1-6}$ alkoxy($C_{1-6}$)alkyl; $C_{1-6}$ alkoxy; cyano; nitro; carboxamido; amidino; amino; halogen; sulfonamido; amidosulfonyl; or hydroxy;

and the pharmaceutically acceptable salts thereof.

An illustration of the invention is any of the methods described above wherein the compound is represented by formula IA

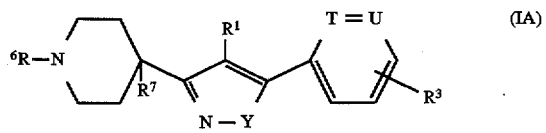

wherein

Y represents oxygen, sulphur or N—R², preferably oxygen or N—R², most preferably oxygen, NH or N-methyl;

one of T and U represents CH and the other represents CH or N, preferably CH;

R³ represents hydrogen, halogen, trifluoromethyl, cyano, nitro, amino, $C_{1-6}$ alkylamino, di($C_{1-6}$)alkylamino, $C_{1-6}$ alkyl, $C_{1-6}$ alkoxy, aryl($C_{1-6}$)alkoxy or $C_{2-6}$ alkylcarbonyl;

R⁶ represents $C_{2-6}$ alkenyl, $C_{3-7}$ cyclo alkyl($C_{1-6}$)alkyl, aryl, aryl($C_{1-6}$)alkyl, aryl($C_{2-6}$)alkenyl or heteroaryl ($C_{1-6}$)alkyl, any of which groups may be optionally substituted with one or more of $C_{1-6}$ alkyl; $C_{1-6}$ alkoxy-$C_{1-6}$ alkyl; $C_{1-6}$ alkoxy; cyano; nitro; carboxamido; amidino; amino; halogen; sulfonamido; amidosulfonyl; or hydroxy; and R⁷ represents hydrogen or methyl, preferably hydrogen; and the pharmaceutically acceptable salts thereof.

In the compounds of formula IA, above, examples of suitable substituents on the group R¹ include hydrogen, methyl, ethyl, methoxy and chloro; suitably, R² represents hydrogen or methyl, especially hydrogen; particular values of R³ include hydrogen, methyl, ethyl, isopropyl, nitro, methoxy and chloro, especially chloro; preferably, R⁶ is selected from allyl, cyclopropylmethyl, cyclohexylmethyl, tetrahydronaphthyl, benzyl, methylbenzyl, chlorobenzyl, dichlorobenzyl, methoxybenzyl, nitrobenzyl, naphthylmethyl, naphthylethyl, phenethyl, methoxyphenethyl, phenylcarbonylmethyl, phenylpropyl, phenylpropenyl, furylmethyl, indolylmethyl, indolylethyl and pyridylethyl.

Exemplifying the invention are any of the methods described above wherein the compound is selected from a compound of formula IB

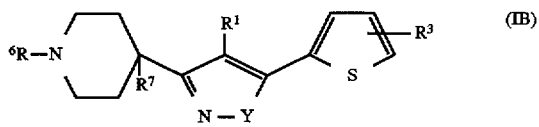

wherein:

Y, R², R³, R⁶ and R⁷ are as defined above for the compounds of formula IA;

and the pharmaceutically acceptable salts thereof.

An example of the invention are any of the methods described above wherein the compound is selected from a compound of formula IC

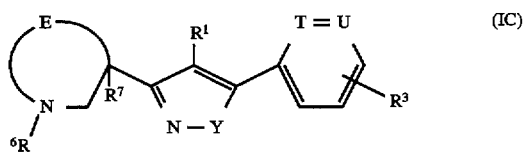

wherein

E represents a linking group of formula —(CH₂)₂— or —(CH₂)₃—; and Y, T, U, R², R³, R⁶ and R⁷ are as defined above for the compounds of formula IA;

and the pharmaceutically acceptable salts thereof.

Illustrating the invention are any of the methods described above wherein the compound is described as 4-aryl and 4-heteroaryl-(2-arylethyl)piperidines of the general structure

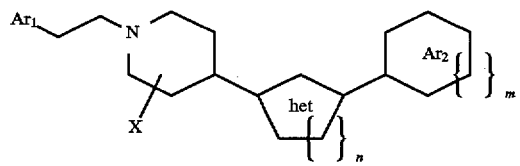

wherein:

Ar1 and Ar2 are each independently selected from an unsubstituted or substituted aromatic, heteroaromatic, or condensed heteroaromatic ring wherein the substituent on the aromatic, heteroaromatic or condensed heteroaromatic ring is selected from amino, $C_{1-6}$ alkoxy, sulfonamido, $C_{1-6}$ alkyl, heteroalkyl or halogen;

m is 0 or 1;

n is 0, 1, or 2;

het is a substituted aromatic or nonaromatic heterocyclic ring wherein the substituent is selected from $C_{1-6}$ alkyl, halogen or $C_{1-6}$ alkoxy; and X is a branched or straight chain aliphatic or halogen substituent;

and the pharmaceutically acceptable salts thereof.

Another illustration of the invention are any of the methods described above wherein the compound is represented by the formula:

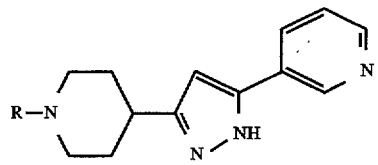

wherein R is selected from:

2-phenylethyl; benzyl; 2-(3-indolyl)ethyl; 2-(1-naphthyl)ethyl; 2-(2,6-dimethoxy)phenoxyethyl; 2-(2-ethoxy)phenoxyethyl; 2-(2-methoxy-phenyl)ethyl; 2-(2-naphthyl)ethyl; 2-(4-methoxyphenyl)ethyl; 2-(3-methoxyphenyl)ethyl; 2-(3-benzothiophen)ethyl; hydrogen; β-tetralin; or 2-(N-benzimidazolone)ethyl;

and the pharmaceutically acceptable salts thereof.

Further illustrating the invention are any of the methods described above wherein the compound is represented by the formula:

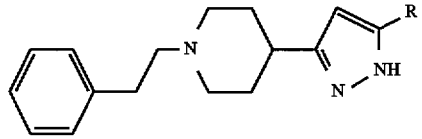

wherein R is selected from 3-pyridyl; 2-pyridyl; 4-pyridyl; phenyl; 3-nitrophenyl; 3-cyanophenyl; or 3-bromophenyl;

and the pharmaceutically acceptable salts thereof.

Another example of the invention are any of the methods described above wherein the compound is represented by the formula:

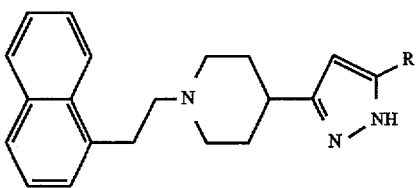

wherein R is selected from 3-pyridyl; 3,4-dichlorophenyl; 3-nitrophenyl; 3-bromophenyl;

3-cyanophenyl; 2-pyridyl; 2-naphthyl; 6-benzsodioxane; 2-furyl;

3-thienyl; 3,4-methylenedioxyphenyl; 4-methoxyphenyl; 4-cyanophenyl;

6-quinolinyl; or 3,4-dimethoxyphenyl;

and the pharmaceutically acceptable salts thereof.

Further exemplifying the invention are any of the methods described above wherein the compound is selected from:

1-(4-chlorobenzyl)-4-[3 -(4-chlorophenyl)-3-hydroxy-1-oxoprop-2-en-1-yl]piperidine;

1-benzyl-4-[3-(4-chlorophenyl)-3-hydroxy-1-oxoprop-2-en-1-yl]piperidine;

1-(4-chlorobenzyl)-4-[3-hydroxy-3-(4-nitrophenyl)-1-oxoprop-2-en-1-yl]piperidine;

4-[3-(4-chlorophenyl)-3-hydroxy-1-oxoprop-2-en-1-yl]-1-(2-phenylethyl)piperidine;

1-benzyl -3-[3-(4-chlorophenyl)-3-hydroxy-1-oxoprop-2-en-1-yl]piperidine;

4-[3-(4-chlorophenyl)-2-methyl-1,3-dioxoprop-1-yl]-1-(2-phenylethyl)piperidine;

1-benzyl-4-[3-hydroxy-1-oxo-3-(2-thienyl)prop-2-en-1-yl]piperidine;

4-[3-hydroxy-1-oxo-3-(3-pyridyl)prop-2-en-1-yl]-1-(2-phenylethyl)piperidine;

3-[1-(4-chlorobenzyl)piperidin-4-yl]-5-(4-chlorophenyl)pyrazole;

3-(1-benzylpiperidin-4-yl)-5-(4-chlorophenyl)pyrazole;

5-(4-chlorophenyl)-3-[1-(4-methylbenzyl)piperidin-4-yl]pyrazole;

5-(4-chlorophenyl)-3-[1-(4-methoxybenzyl)piperidin-4-yl]pyrazole;

5-(4-chlorophenyl)-3-[1-(prop-2-en-1-yl)piperidin-4-yl]pyrazole;

5-(4-chlorophenyl)-3-[1-(4-nitrobenzyl)piperidin-4-yl]pyrazole;

3-[1-(4-chlorobenzyl)piperidin-4-yl]-5-phenylpyrazole;

3-[1-(4-chlorobenzyl)piperidin-4-yl]-5-(2-thienyl)pyrazole;

3-[1-(4-chlorobenzyl)piperidin-4-yl]-5-(4-isopropylphenyl)pyrazole;

3-[1-(4-chlorobenzyl)piperidin-4-yl]-5-(4-methoxyphenyl)pyrazole;

5-(4-chlorophenyl)-3-(1-cyclohexylmethylpiperidin-4-yl)pyrazole;

5-(4-chlorophenyl)-3-[1-(2-phenylethyl)piperidin-4-yl]pyrazole;

5-(4-chlorophenyl)-3-[1-(3,4-dichlorobenzyl)piperidin-4-yl]pyrazole;

3-[1-(4-chlorobenzyl)piperidin-4-yl]-5-(3-chlorophenyl)pyrazole;

3-[1-(3-chlorobenzyl)piperidin-4-yl]-5-(4-chlorophenyl)pyrazole;

5-[1-(4-chlorobenzyl)piperidin-4-yl]-3-(4-chlorophenyl)-1-methylpyrazole;

3-[1-(4-chlorobenzyl)piperidin-4-yl]-5-(4-chlorophenyl)-1-methylpyrazole;

3-[1-(4-chlorobenzyl)piperidin-4-yl]-5-(2-chlorophenyl)pyrazole;

3-(1-benzylpiperidin-4-yl)-5-phenylpyrazole;

3-[1-(4-chlorobenzyl)piperidin-4-yl]-5-(4-chlorophenyl)isoxazole;

5-[1-(4-chlorobenzyl)piperidin-4-yl]-3-(4-chlorophenyl)isoxazole;

3-[1-(4-chlorobenzyl)piperidin-4-yl]-5-(2-methoxyphenyl)pyrazole;

5-(4-chlorophenyl)-3-[1-(2-methylbenzyl)piperidin-4-yl]pyrazole;

5-(4-chlorophenyl)-3-[1-(3-nitrobenzyl)piperidin-4-yl]pyrazole;

5-(4-chlorophenyl)-3-[1-(3-methylbenzyl)piperidin-4-yl]pyrazole;

5-(4-chlorophenyl)-3-[1-(2-nitrobenzyl)piperidin-4-yl]pyrazole;

3-[1-(4-chlorobenzyl)piperidin-4-yl]-4-methyl-5-phenylpyrazole;

3-[1-(2-chlorobenzyl)piperidin-4-yl]-5-(4-chlorophenyl)pyrazole;

5-(4-chlorophenyl)-3-(1-cyclopropylmethylpiperidin-4-yl)pyrazole;

3-(1-benzylpiperidin-4-yl)-5-(4-chlorophenyl)-4-methylpyrazole;

5-(4-chlorophenyl)-3-[1-(2-naphthylmethyl)piperidin-4-yl]pyrazole;

5-(4-chlorophenyl)-3-[1-(3-phenylpropyl)piperidin-4-yl]pyrazole;

5-(4-chlorophenyl)-3-[1-(3-methoxybenzyl)piperidin-4-yl]pyrazole;

3-[1-(2-phenylethyl)piperidin-4-yl]-5-(2-pyridyl)pyrazole;

3-(1-benzyl-4-methylpiperidin-4-yl)-5-(4-chlorophenyl)pyrazole;

5-(4-chlorophenyl)-3-[1-(indol-3-ylmethyl)piperidin-4-yl]pyrazole;

5-(4-chlorophenyl)-4-methyl-3-[1-(2-phenylethyl)piperidin-4-yl]pyrazole;

3-(1-benzylpiperidin-3-yl)-5-(4-chlorophenyl)pyrazole;

3-(1-benzylpyrrolidin-3-yl)-5-(4-chlorophenyl)pyrazole;

3-(1-benzylpiperidin-4-yl)-5-(2-thienyl)isoxazole;

5-(1-benzylpiperidin-4-yl)-3-(2-thienyl)isoxazole;

5-(4-chlorophenyl)-3-[1-(2-phenylethyl)piperidin-4-yl]isoxazole;

3-(1-benzylpiperidin-4-yl)-5-(4-chlorophenyl)isoxazole;

3-(4-chlorophenyl)-4-methyl -5-[1-(2-phenylethyl)piperidin-4-yl]isoxazole;

5-(4-chlorophenyl)-4-methyl-3-[1-(2-phenylethyl)piperidin-4-yl]isoxazole;

3-(1-benzylpiperidin-4-yl)-5-(4-chlorophenyl)-4-ethylpyrazole;

5-(1-benzylpiperidin-4-yl)-3-(4-chlorophenyl)-1,4-dimethylpyrazole;

3-(1-benzylpiperidin-4-yl)-5-(4-chlorophenyl)-1,4-dimethylpyrazole;

4-methoxy-5-phenyl-3-[1-(2-phenylethyl)piperidin-4-yl]pyrazole;

5-(4-chlorophenyl)-3-[1-(3-E-phenylprop-2-en-1-yl)piperidin-4-yl]pyrazole;

5-(4-chlorophenyl)-3-[1-(1-naphthylmethyl)piperidin-4-yl]pyrazole;

3-[1-(2-furylmethyl)piperidin-4-yl]-4-methyl-5-phenylpyrazole;

3-[1-(2-(4-methoxyphenyl)ethyl)piperidin-4-yl]-4-methyl-5-phenylpyrazole;

4-methyl-3-[1-(2-oxo-2-phenylethyl)piperidin-4-yl]-5-phenylpyrazole;

4-methyl-5-phenyl-3-[1-(2-(3-pyridyl)ethyl)piperidin-4-yl]pyrazole;

5-(4-chlorophenyl)-3-[1-(1,2,3,4-tetrahydronaphth-2-yl)
  piperidin-4-yl]pyrazole;
4-chloro -5-(4-chlorophenyl)-3-[1-(2-phenylethyl)
  piperidin-4-yl]pyrazole;
1-(2-(1-Naphthyl)ethyl)-4-(5-(pyridin-3-yl)pyrazol-3-yl)
  piperidine;
1-(2-(3-Indolyl)ethyl)-4-(5-(pyridin-3-yl)pyrazol-3-yl)
  piperidine;
1-(2-(1-Naphthyl)ethyl)-4-(5-(3,4-dichlorophenyl)pyrazol-
  3-yl)piperidine;
1-(2-(1-Naphthyl)ethyl)-4-(5-(3,4-dimethoxyphenyl)
  pyrazol-3-yl)piperidine;
1-(2-(1-Naphthyl)ethyl)-4-(5-(3-nitrophenyl)pyrazol-3-yl)
  piperidine;
1-(2-Phenylethyl)-4-(5-(3-nitrophenyl)pyrazol-3-yl)
  piperidine;
1-(2-(1-Naphthyl)ethyl)-4-(5-(3-bromophenyl)pyrazol-3-yl)
  piperidine;
1-(2-Phenylethyl)-4-(5-(3-bromophenyl)pyrazol-3-yl)
  piperidine;
1-(2-(1-Naphthyl)ethyl)-4-(5-(3-cyanophenyl)pyrazol-3-yl)
  piperidine;
1-(2-Phenylethyl)-4-(5-(3-cyanophenyl)pyrazol-3-yl)
  piperidine;
1-(2-(1-Naphthyl)ethyl)-4-(5-(4-cyanophenyl)pyrazol-3-yl)
  piperidine;
1-(2-(1-Naphthyl)ethyl)-4-(5-(2-pyridyl)pyrazol-3-yl)
  piperidine;
1-(2-(1-Naphthyl)ethyl)-4-(5-(2-naphthyl)pyrazol-3-yl)
  piperidine;
1-(2-(1-Naphthyl)ethyl)-4-(5-(benzodioxan-6-yl)pyrazol-3-
  yl)piperidine;
1-(2-(1-Naphthyl)ethyl)-4-(5-(2-furyl)pyrazol-3-yl)
  piperidine;
1-(2-(1-Naphthyl)ethyl)-4-(5-(3-thienyl)pyrazol-3-yl)
  piperidine;
1-(2-(1-Naphthyl)ethyl)-4-(5-(3,4-methylenedioxyphenyl)
  pyrazol-3-yl)piperidine;
1-(2-(1-Naphthyl)ethyl)-4-(5-(4-methoxyphenyl)pyrazol-3-
  yl)piperidine;
1-(2-(1-Naphthyl)ethyl)-4-(5-(6-quinolinyl)pyrazol-3-yl)
  piperidine;
1-(2-(2,6-Dimethoxyphenoxy)ethyl)-4-(5-(pyridin-3-yl)
  pyrazol-3-yl)piperidine;
1-(2-(2-Ethoxyphenoxy)ethyl)-4-(5-(pyridin-3-yl)pyrazol-
  3-yl)piperidine;
1-(2-(2-Methoxyphenyl)ethyl)-4-(5-(pyridin-3-yl)pyrazol-
  3-yl)piperidine;
1-(2-(2-Naphthyl)ethyl)-4-(5-(pyridin-3-yl)pyrazol-3-yl)
  piperidine;
1-(2-(4-Methoxyphenyl)ethyl)-4-(5-(pyridin-3-yl)pyrazol-
  3-yl)piperidine;
1-(2-(3-Methoxyphenyl)ethyl)-4-(5-(pyridin-3-yl)pyrazol-
  3-yl)piperidine;
1-(2-(Benzothiophen-3-yl)ethyl)-4-(5-(pyridin-3-yl)
  pyrazol-3-yl)piperidine;
1-(2-(N-benzimidazol-2-one)ethyl)-4-(5-(pyridin-3-yl)
  pyrazol-3-yl)piperidine;
1-(2-(3-Indolyl)ethyl)-4-(5-(benzodioxan-6-yl)pyrazol-3-
  yl)piperidine;
1-(2-(3-Benzofuryl)ethyl)-4-(5-(benzodioxan-6-yl)pyrazol-
  3-yl)piperidine;
1-(Tetralin-2-yl)-4-[5-(pyridin-3-yl)]pyrazole-3-yl]
  piperidine;
1-(2-(1-Naphthyl)ethyl)-4-(3-(1,4-benzodioxan-6-yl)
  isoxazol-5-yl)piperidine; or
1-(2-(1-Naphthyl)ethyl)-4-(5-(1,4-benzodioxan-6-yl)
  isoxazol-3-yl)piperidine;

and the pharmaceutically acceptable salts thereof.

More particularly illustrating the invention are any of the methods described above wherein any of the compounds described above are administered in combination with a testosterone 5-alpha reductase inhibitor. Preferably, the testosterone 5-alpha reductase inhibitor is finasteride.

More specifically exemplifying the invention is a compound represented by formula I

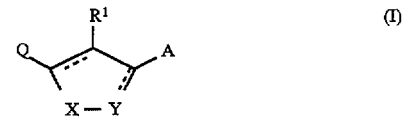

wherein the broken lines represent two non-adjacent double bonds in any position within the five-membered ring, it being understood that bonds to O, S and N—$R^2$ are single bonds;

one of X and Y represents nitrogen, and the other of X and Y represents oxygen, sulphur or N—$R^2$;

Q represents a substituted five- or six-membered monocyclic heteroaliphatic ring which contains one nitrogen atom as the sole heteroatom and is linked to the five-membered heteroatomic ring containing the moieties X and Y via a carbon atom;

$R^1$ is selected from hydrogen, halogen, $C_{1-6}$ alkyl, hydroxy or $C_{1-6}$ alkoxy;

$R^2$ is selected from hydrogen or $C_{1-6}$ alkyl; and

A represents a group of formula (iv):

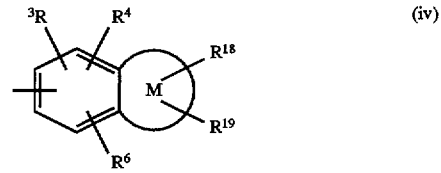

in which $R^3$, $R^4$ and $R^5$ are each independently selected from hydrogen, hydrocarbon, a heterocyclic group, halogen, cyano, trifluoromethyl, nitro, —$OR^a$, —$SR^a$, —$SOR^a$, —$SO_2R^a$, —$SO_2NR^aR^b$, —$NR^aR^b$, —$NR^aCOR^b$, —$NR^aCO_2R^b$, —$COR^a$, —$CO_2R^a$ or —$CO_2NR^aR^b$;

$R^a$ and $R^b$ are each independently selected from hydrogen, hydrocarbon or a heterocyclic group;

the ring M is an additional ring or ring system such that the entire structure (iv) is a dicyclic or polycyclic aromatic or heteroaromatic ring system; and $R^{18}$ and $R^{19}$ are each independently selected from $C_{1-6}$ alkyl; $C_{1-6}$ alkoxy($C_{1-6}$)alkyl; $C_{1-6}$ alkoxy; cyano; nitro; carboxamido; amidino; amino; halo; sulfonamido; amidosulfonyl; hydrogen or hydroxy;

and the pharmaceutically acceptable salts thereof.

Another example of the invention is any of the compounds described above wherein the group A is selected from benzodioxane; methylenedioxyphenyl; indane; 2,3,-dihydrobenzofuran; 2,7-dihydroisobenzofuran; 1-naphthyl; 2-naphthyl; benzothiophene; benzofuran; indole; quinoline; isoquinoline; indazole; benzisoxazole; benzthiazole; benzimidazol(on)e; thiophene; furan; or pyridine;

and the pharmaceutically acceptable salts thereof.

More specifically illustrating the invention is any of the compounds described above wherein the group Q is selected from Qa to Qe:

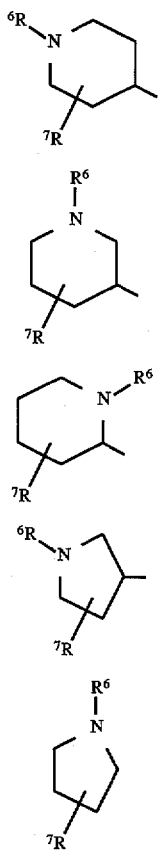

wherein one of $R^6$ and $R^7$ represents hydrocarbon, an ether or a heterocyclic group, and the other of $R^6$ and $R^7$ represents hydrogen, hydrocarbon, an ether or a heterocyclic group;

and the pharmaceutically acceptable salts thereof.

Another illustration of the invention is any of the compounds described above wherein $R^6$ is $C_{0-6}$ alkyl substituted with a monocyclic or polycyclic aromatic or heteroaromatic group selected from:

phenyl; 1-naphthyl; 2-naphthyl; benzothiophene; benzofuran; indole; quinoline; isoquinoline; indazole; benzisoxazole; benzimidazol(on)e; thiophene; furan; or pyridine; wherein the monocyclic or polycyclic aromatic or heteroaromatic group is optionally substituted with one or more of $C_{1-6}$ alkyl; $C_{1-6}$ alkoxy-$C_{1-6}$ alkyl; $C_{1-6}$ alkoxy; cyano; nitro; carboxamido; amidino; amino; halo; sulfonamido; amidosulfonyl; or hydroxy;

and the pharmaceutically acceptable salts thereof.

More particularly exemplifying the invention is a compound selected from:

1-(2-(1-Naphthyl)ethyl)-4-(5-(pyridin-3-yl)pyrazol-3-yl) piperidine;
1-(2-(3-Indolyl)ethyl)-4-(5-(pyridin-3-yl)pyrazol-3-yl) piperidine;
1-(2-(1-Naphthyl)ethyl)-4-(5-(3,4-dichlorophenyl)pyrazol-3-yl)piperidine;
1-(2-(1-Naphthyl)ethyl)-4-(5-(3,4-dimethoxyphenyl) pyrazol-3-yl)piperidine;
1-(2-(1-Naphthyl)ethyl)-4-(5-(3-nitrophenyl)pyrazol-3-yl) piperidine;
1-(2-Phenylethyl)-4-(5-(3-nitrophenyl)pyrazol-3-yl) piperidine;
1-(2-(1-Naphthyl)ethyl)-4-(5-(3-bromophenyl )pyrazol-3-yl)piperidine;
1-(2-Phenylethyl)-4-(5-(3-bromophenyl)pyrazol-3-yl) piperidine;
1-(2-(1-Naphthyl)ethyl)-4-(5-(3-cyanophenyl)pyrazol-3-yl) piperidine;
1-(2-Phenylethyl)-4-(5-(3-cyanophenyl)pyrazol-3-yl) piperidine;
1-(2-(1-Naphthyl)ethyl)-4-(5-(4-cyanophenyl )pyrazol-3-yl )piperidine;
1-(2-(1-Naphthyl)ethyl)-4-(5-(2-pyridyl)pyrazol-3-yl) piperidine;
1-(2-(1-Naphthyl)ethyl)-4-(5-(2-naphthyl)pyrazol-3-yl) piperidine;
1-(2-(1-Naphthyl)ethyl)-4-(5-(benzodioxan-6-yl)pyrazol-3-yl)piperidine;
1-(2-(1-Naphthyl)ethyl)-4-(5-(2-furyl)pyrazol-3-yl) piperidine;
1-(2-(1-Naphthyl)ethyl)-4-(5-(3-thienyl)pyrazol-3-yl) piperidine;
1-(2-(1-Naphthyl)ethyl)-4-(5-(3,4-methylenedioxyphenyl) pyrazol-3-yl)piperidine;
1-(2-(1-Naphthyl)ethyl)-4-(5-(4-methoxyphenyl)pyrazol-3-yl)piperidine;
1-(2-(1-Naphthyl)ethyl)-4-(5-(6- quinolinyl)pyrazol-3-yl) piperidine;
1-(2-(2,6-Dimethoxyphenoxy)ethyl)-4-(5-(pyridin-3-yl) pyrazol-3-yl)piperidine;
1-(2-(2-Ethoxyphenoxy)ethyl)-4-(5-(pyridin-3-yl)pyrazol-3-yl)piperidine;
1-(2-(2-Methoxyphenyl)ethyl)-4-(5-(pyridin-3-yl)pyrazol-3-yl)piperidine;
1-(2-(2-Naphthyl)ethyl)-4-(5-(pyridin-3-yl)pyrazol-3-yl) piperidine;
1-(2-(4-Methoxyphenyl)ethyl)-4-(5-(pyridin-3-yl)pyrazol-3-yl)piperidine;
1-(2-(3- Methoxyphenyl)ethyl)-4-(5-(pyridin -3-yl)pyrazol-3-yl)piperidine;
1-(2-(Benzothiophen-3-yl)ethyl)-4-(5-(pyridin-3-yl) pyrazol-3-yl)piperidine;
1-(2-(N-benzimidazol-2-one)ethyl)-4-(5-(pyridin-3-yl) pyrazol-3-yl)piperidine;
1-(2-(3-Indolyl)ethyl)-4-(5-(benzodioxan-6-yl)pyrazol-3-yl)piperidine;
1-(2-(3-Benzofuryl)ethyl)-4-(5-(benzodioxan-6-yl)pyrazol-3-yl)piperidine;
1-(Tetralin-2-yl)-4-[5-(pyridin-3-yl)[pyrazole-3-yl] piperidine;
1-(2-(1-Naphthyl)ethyl)-4-(3-(1,4-benzodioxan-6-yl) isoxazol-5-yl)piperidine; or
1-(2-(1-Naphthyl)ethyl)-4-(5-(1,4-benzodioxan-6-yl) isoxazol-3-yl)piperidine;

and the pharmaceutically acceptable salts thereof.

An additional illustration of the invention is a pharmaceutical composition comprising a pharmaceutically acceptable carrier and a therapeutically effective amount of any of the compounds described above. Still another example of the invention is the pharmaceutical composition which further comprises a therapeutically effective amount of a 5-alpha reductase inhibitor. Preferably, the testosterone 5-alpha reductase inhibitor is a type 1, a type 2, both a type 1 and a type 2 (i.e., a three component combination comprising any of the compounds described above combined with both a type 1 testosterone 5-alpha reductase inhibitor and a type 2 testosterone 5-alpha reductase inhibitor), or a dual type 1 and type 2 testosterone 5-alpha reductase inhibitor. More preferably, the testosterone 5-alpha reductase inhibitor is a type 2 testosterone 5-alpha reductase inhibitor. Most preferably, the testosterone 5-alpha reductase inhibitor is finasteride.

DETAILED DESCRIPTION OF THE INVENTION

The present invention relates to treatment of urinary obstruction caused by benign prostatic hypertropy (BPH) with selective alpha-1a adrenoceptor antagonist compounds. This invention has the advantage over non-selective alpha-1 adrenoceptor antagonists of reduced side effects related to peripheral adrenergic blockade. Such side effects include hypotension, syncope, lethargy, etc.

Representative compounds of the present invention exhibit high selectivity for the human alpha1a adrenergic receptor. One implication of this selectivity is that these compounds display selectivity for lowering intraurethral pressure without substantially affecting diastolic blood pressure.

Representative compounds of this invention display submicromolar affinity for the human alpha1a adrenergic receptor subtype while displaying at least ten-fold lower affinity for the human alpha1d and alpha1b adrenergic receptor subtypes, and many other G-protein coupled human receptors. Particular representative compounds of this invention exhibit nanomolar and subnanomolar affinity for the human alpha1a adrenergic receptor subtype while displaying at least 30 fold lower affinity for the human alpha1d and alpha1b adrenergic receptor subtypes, and many other G-protein coupled human receptors. Preferred compounds of this invention exhibit Ki's for human alpha1a adrenergic receptors which are more than 100 fold lower than for the human alpha1d adrenergic receptor, while exhibiting greater than 30 fold selectivity for the human alpha1a adrenergic receptor over all other human G-protein coupled receptors tested (including serotonin, dopamine, alpha 2 adrenergic, beta adrenergic or muscarinic receptors).

In the compounds of the present invention described above, the five-membered heteroaromatic ring containing the moieties X and Y represented by formula I above may be a substituted isoxazole, isothiazole or pyrazole ring, preferably isoxazole or pyrazole.

The monocyclic heteroaliphatic ring Q in the compounds of formula I above represents a substituted pyrrolidyl or piperidyl moiety linked through carbon. Examples of suitable rings include the moieties of formula Qa to Qe:

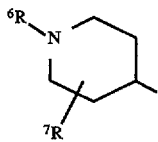
(Qa)

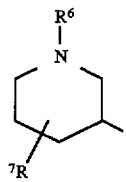
(Qb)

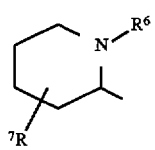
(Qc)

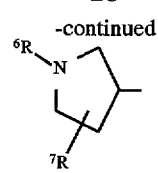
(Qd)

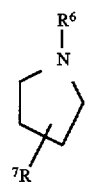
(Qe)

wherein one of $R^6$ and $R^7$ represents hydrocarbon, an ether or a heterocyclic group, and the other of $R^6$ and $R^7$ represents hydrogen, hydrocarbon, an ether or a heterocyclic group.

Particular monocyclic heteroaliphatic rings represented by the substituent Q in formula I include the rings of structure Qa, Qb and Qd above, especially Qa.

The term "hydrocarbon," as used herein, includes straight-chained, branched and cyclic groups containing up to 18 carbon atoms, suitably up to 15 carbon atoms, and conveniently up to 12 carbon atoms. Suitable hydrocarbon groups include $C_{1-6}$ alkyl, $C_{2-6}$ alkenyl, $C_{2-6}$ alkynyl, $C_{3-7}$ cycloalkyl, $C_{3-7}$ cycloalkyl($C_{1-6}$)alkyl, aryl, aryl($C_{1-6}$)alkyl, aryl($C_{2-6}$)alkenyl and aryl($C_{2-6}$)alkynyl.

The expression "a heterocyclic group," as used herein, includes monocyclic and polycyclic groups containing up to 18 carbon atoms and at least one heteroatom preferably selected from oxygen, nitrogen and sulphur. The heterocyclic group suitably contains up to 15 carbon atoms and conveniently up to 12 carbon atoms, and is preferably linked through carbon. Examples of suitable heterocyclic groups include $C_{3-7}$ heterocycloalkyl, $C_{3-7}$ heterocycloalkyl($C_{1-6}$) alkyl, heteroaryl and heteroaryl($C_{1-6}$)alkyl groups.

The term "an ether," as used herein, refers to an oxygen containing ether substituted with $C_{1-6}$ alkyl, aryl, or heteroaryl groups or a combination of any two; i.e., R—O—R' wherein R and R' are independently alkyl, aryl or heteroaryl.

Suitable alkyl groups include straight-chained and branched alkyl groups containing from 1 to 6 carbon atoms. Typical examples include methyl and ethyl groups, and straight-chained or branched propyl and butyl groups. Particular alkyl groups are methyl, ethyl, isopropyl and t-butyl.

Suitable alkenyl groups include straight-chained and branched alkenyl groups containing from 2 to 6 carbon atoms. Typical examples include vinyl and allyl groups.

Suitable alkynyl groups include straight-chained and branched alkynyl groups containing from 2 to 6 carbon atoms. Typical examples include ethynyl and propargyl groups.

Suitable cycloalkyl groups include groups containing from 3 to 7 carbon atoms. Particular cycloalkyl groups are cyclopropyl and cyclohexyl.

Particular $C_{3-7}$ cycloalkyl($C_{1-6}$)alkyl groups include cyclopropylmethyl and cyclohexylmethyl.

Particular aryl groups include phenyl, naphthyl and tetrahydronaphthyl; particular aromatic ring systems include phenyl and naphthyl.

Particular aryl($C_{1-6}$)alkyl groups include benzyl, naphthylmethyl, naphthylethyl, phenethyl and phenylpropyl. Particular aryl($C_{1-6}$)alkenyl groups include phenylethenyl and phenylpropenyl.

A particular aryl($C_{2-6}$)alkynyl group is phenylethynyl.

The term "heteroalkyl," as used herein refers to $C_{1-6}$ alkylthio, $C_{1-6}$ alkylamino, $C_{1-6}$ alkoxy, $C_{1-6}$ alkylthio ($C_{1-6}$)

alkyl, $C_{1-6}$ alkylamino($C_{1-6}$)alkyl, and $C_{1-6}$ alkoxy($C_{1-6}$) alkyl, with alkyl being branched or straight chain. Thio can be —S—, —S(O)— and —S(O)$_2$—; amino can be mono or disubstituted or —NH$_2$—.

The term "aliphatic," as used herein refers to acyclic open chain carbon compounds such as alkanes, alkenes and alkynes.

Suitable heterocycloalkyl groups include azetidinyl, pyrrolidyl, piperidyl, piperazinyl and morpholinyl groups.

Suitable heteroaryl or heteroaromatic groups include pyridyl, quinolyl, isoquinolyl, pyridazinyl, pyrimidinyl, pyrazinyl, pyranyl, furyl, benzofuryl, dibenzofuryl, thienyl, benzthienyl, indolyl, imidazolyl, oxadiazolyl and thiadiazolyl groups.

Particular heteroaryl($C_{1-6}$)alkyl groups include pyridylmethyl, furylmethyl, indolylmethyl, pyrazinylmethyl and pyridylethyl.

The hydrocarbon and heterocyclic groups may in turn be optionally substituted by one or more groups selected from $C_{1-6}$ alkyl, adamantyl, phenyl, halogen, $C_{1-6}$ haloalkyl, $C_{1-6}$ aminoalkyl, trifluoromethyl, hydroxy, $C_{1-6}$ alkoxy, aryloxy, keto, $C_{1-3}$ alkylenedioxy, nitro, cyano, carboxy, $C_{2-6}$ alkoxycarbonyl, $C_{2-6}$ alkoxycarbonyl($C_{1-6}$)alkyl, $C_{2-6}$ alkylcarbonyloxy, arylcarbonyloxy, $C_{2-6}$ alkylcarbonyl, arylcarbonyl, $C_{1-6}$ alkylthio, $C_{1-6}$ alkylsulphinyl, $C_{1-6}$ alkylsulphonyl, arylsulphonyl, —NR'R''', —NR'COR''', —NR'CO$_2$R''', —NR'SO$_2$R''', —CH$_2$NR'SO$_2$R''', —NHCONR'R''', —CONR'R''', —SO$_2$NR'R''' and —CH$_2$SO$_2$NR'R''', in which R' and R''' independently represent hydrogen, $C_{1-6}$ alkyl, aryl or aryl($C_{1-6}$)alkyl.

The term "halogen," as used, herein includes fluorine, chlorine, bromine and iodine, especially chlorine.

Preferably, the heterocyclic group constituting $R^6$ or $R^7$ is a monocyclic or polycyclic aromatic or heteroaromatic group such as, but are not limited to:

phenyl; 1-naphthyl; 2-naphthyl; benzothiophene; benzofuran; indole; quinoline; isoquinoline; indazole; benzisoxazole; benzimidazol(on)e; thiphene; furan; and pyridine; each of which may or may not be substituted with one or more of $C_{1-6}$ alkyl; alkoxyalkyl; alkoxy; cyano; nitro; carboxamido; amidino; amino; halo; sulfonamido; amidosulfonyl; and hydroxy.

Suitably, the substituent $R^1$ represents hydrogen, halogen, $C_{1-6}$ alkyl or $C_{1-6}$ alkoxy, especially hydrogen, methyl, ethyl, methoxy or chloro.

Suitably, the substituent $R^2$ represents hydrogen or methyl, especially hydrogen.

Suitably, Z is sulphur.

Suitable values for the substituents $R^3$, $R^4$ and $R^5$ include hydrogen, halogen, trifluoromethyl, cyano, nitro, amino, $C_{1-6}$ alkylamino, di($C_{1-6}$)alkylamino, $C_{1-6}$ alkyl, $C_{1-6}$ alkoxy, aryl($C_{1-6}$)alkoxy and $C_{2-6}$ alkylcarbonyl. Particular values include hydrogen, methyl, ethyl, isopropyl, nitro, methoxy and chloro. Suitably, at least one of $R^3$, $R^4$ and $R^5$ is other than hydrogen, especially chloro.

Suitable values for the substituents $R^6$ and $R^7$ include $C_{1-6}$ alkyl, $C_{2-6}$ alkenyl, $C_{3-7}$ cycloalkyl($C_{1-6}$)alkyl, aryl, aryl ($C_{1-6}$) alkyl, aryl($C_{2-6}$)alkenyl and heteroaryl($C_{1-6}$)alkyl, any of which groups may be optionally substituted. In addition, one of $R^6$ and/or $R^7$ may represent hydrogen. Examples of suitable substituents on the groups $R^6$ and/or $R^7$ include $C_{1-6}$ alkyl, halogen, $C_{1-6}$ alkoxy, keto and nitro.

Particular values of $R^6$ and $R^7$ include hydrogen, methyl, allyl, cyclopropylmethyl, cyclohexylmethyl, tetrahydronaphthyl, benzyl, methylbenzyl, chlorobenzyl, dichlorobenzyl, methoxybenzyl, nitrobenzyl, naphthylmethyl, naphthylethyl, phenethyl, methoxyphenethyl, phenylcarbonylmethyl, phenylpropyl, phenylpropenyl, furylmethyl, indolylmethyl, indolylethyl and pyridylethyl, provided that at least one of $R^6$ and $R^7$ is other than hydrogen. Suitably, one of $R^6$ and $R^7$ represents hydrogen, and the other of $R^6$ and $R^7$ is other than hydrogen. Preferably, $R^7$ represents hydrogen and $R^6$ is other than hydrogen.

The compounds of formula I above may be prepared by a process which comprises reacting a compound of formula II with a compound of formula III:

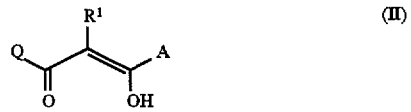

$$H_2N-X^aH \quad (III)$$

wherein Q, $R^1$ and A are as defined above, and $X^a$ represents oxygen, sulphur or N—$R^2$ in which $R^2$ is as defined above; followed, if necessary, by separation of the resulting mixture of isomers by conventional means.

The reaction is conveniently carried out by stirring the reactants in a suitable solvent, for example a mixture of N,N-dimethylformamide and methanol, optionally in the presence of a non-nucleophilic base such as ethyldiisopropylamine, suitably at room temperature. Depending upon the nature of the reactants and of the chosen reaction conditions, the reaction may afford the desired product in a single step, or may proceed via the intermediate IV:

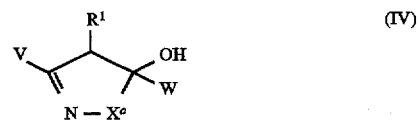

wherein one of V and W represents the group Q and the other represents the group A; and Q, A, $R^1$ and $X^a$ are as defined above.

The intermediate IV can be converted into the corresponding product of formula I by dehydration. This is conveniently effected by converting the hydroxy group into a leaving group, suitably by treatment with methanesulphonyl chloride in dichloromethane at 0° C., and treating the resulting compound, ideally in situ, with a base such as triethylamine.

As indicated above, the overall reaction between compounds II and III will usually give rise to a mixture of isomeric products of formula I, in one of which X represents nitrogen and Y represents oxygen, sulphur or N—$R^2$, and in the other of which the X and Y moieties are reversed. For this reason, it will generally be necessary to separate the mixture of isomers obtained therefrom by conventional methods such as chromatography.

The compounds of formula II above are active in their own s right as ligands for the human alpha1a adrenergic receptor. These compounds, and salts thereof and prodrugs thereof, accordingly represent a further aspect of the present invention.

As will be appreciated, the compounds of formula II as depicted above will generally exist in equilibrium with their other tautomeric forms, including structures (A) and (B):

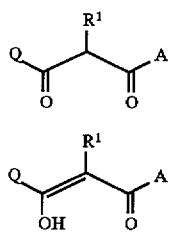

wherein Q, R¹ and A are as defined above. It is to be understood that all tautomeric forms of the compounds of formula II, as well as all possible mixtures thereof, are included within the scope of the present invention.

A sub-class of compounds according to the invention is represented by the compounds of formula IIA, and salts and prodrugs thereof:

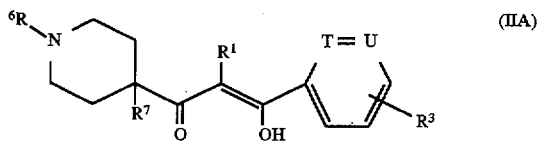

wherein

T, U, R¹, R³, R⁶ and R⁷ are as defined with reference to formula IA above.

Another sub-class of compounds according to the invention is represented by the compounds of formula IIB, and salts and prodrugs thereof:

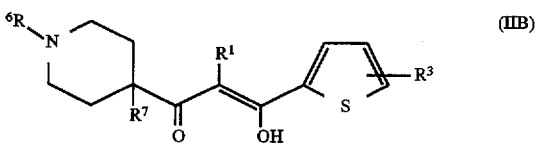

wherein R¹, R³, R⁶ and R⁷ are as defined with reference to formula IA above.

An additional sub-class of compounds according to the invention is represented by the compounds of formula IIC, and salts and prodrugs thereof:

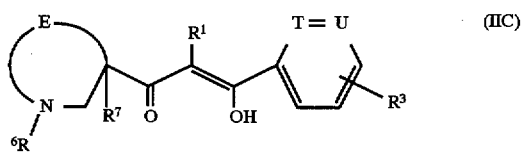

wherein

T, U, R¹, R³, R⁶ and R⁷ are as defined with reference to formula IA above; and

E is as defined with reference to formula IC above.

The compounds of formula II as defined above may be prepared by reacting a carboxylic acid of formula V, or an activated derivative thereof, with two equivalents of a metal enolate of formula VI:

$$Q^1-CO_2H \quad (V)$$

wherein R¹ and A are as defined above, Q¹ corresponds to the moiety Q as defined above or represents a precursor thereto protected on the nitrogen atom, and M represents a metal capable of providing a suitable counterion for the enolate anion; followed, where required, by removal of the N-protecting group from the moiety Q¹; and subsequently, if necessary, attachment to the nitrogen atom thereby deprotected of an appropriate substituent by standard means to afford a product containing the desired moiety Q.

For example, the substituent Q¹ in compound V may represent a moiety of formula Qa to Qe as defined above, in which R⁷ is hydrogen and R⁶ represents an N-protecting group. Once the reaction between compounds V and VI is complete, the N-protecting group must be removed, and the desired group R⁶ subsequently attached, by conventional methods.

The metal M is suitably an alkali metal, especially lithium.

The activated derivative of the carboxylic acid V is suitably the compound formed by reaction between the carboxylic acid V and 1,1'-carbonyldiimidazole, conveniently in tetrahydrofuran at room temperature.

Where the substituent Q¹ represents a precursor to the moiety Q protected on the nitrogen atom, the N-protecting group is suitably an alkoxycarbonyl moiety such as t-butoxycarbonyl (BOC), in which case the N-protecting group can conveniently be removed subsequently as necessary by treatment under acidic conditions, e.g. stirring in hydrochloric acid or trifluoroacetic acid.

The reaction between compound V, or the activated derivative thereof, and compound VI is suitably carried out in a solvent such as tetrahydrofuran, commencing at −78° C. with warming to 0° C.

The metal enolate of formula VI is ideally prepared by reacting the corresponding carbonyl compound of formula VII:

wherein R¹ and A are as defined above; with a non-nucleophilic base such as lithium diisopropylamide, suitably in tetrahydrofuran at −78° C.

In an alterative process, the compounds of formula I above wherein X represents nitrogen, Y is N—R², R¹ is hydrogen and Q represents a group of formula Qa as defined above may be prepared by reacting a compound of formula VIII:

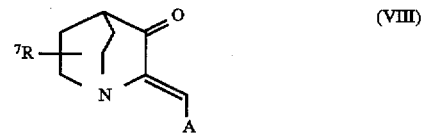

wherein A and R⁷ are as defined above; with hydrazine hydrate; followed by attachment of the groups R² and/or R⁶, where these are required to be other than hydrogen, by standard carbon-nitrogen bond-forming reactions.

The reaction of compound VIII with hydrazine hydrate is advantageously effected in the presence of ethylene glycol and a strong base such as potassium hydroxide, suitably commencing at 110° C. with warming to the reflux temperature of the reaction mixture.

The method whereby the groups R² and/or R⁶ are attached to the product obtained from any of the above-described processes will suitably comprise a standard carbon-nitrogen bond-forming reaction known from the art, such as N-alkylation. By way of example, a compound wherein R⁶ is hydrogen initially obtained may conveniently be N-benzylated by treatment with a benzyl halide, e.g. benzyl bromide, typically under basic conditions, e.g. using triethylamine in a mixture of dichloromethane and N,N-dimethylformamide, suitably at room temperature, to afford a product wherein $R^6$ is benzyl.

The intermediates of formula VIII above may be prepared by condensing an aldehyde of formula A-CHO with a suitable quinuclidin-3-one derivative of formula IX:

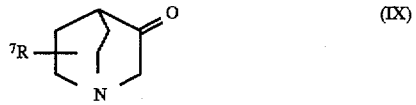

wherein A and $R^7$ are as defined above. The reaction is conveniently carried out in a solvent such as ethanol, advantageously in the presence of a strong base such as sodium hydroxide, suitably by heating the reaction mixture at reflux.

Where they are not commercially available, the starting materials of formula III, V, VII, IX and A-CHO may be prepared by standard methods well known from the art.

It will be appreciated that any compound of formula I or formula II initially obtained from any of the above processes may, where appropriate, subsequently be elaborated into a further desired compound of formula I or formula II using techniques known from the art. For example, as alluded to above, a compound of formula I wherein $R^2$ is hydrogen initially obtained may be converted into a compound of formula I wherein $R^2$ is other than hydrogen by means of conventional N-alkylation methodology.

Where the processes for the preparation of the compounds according to the invention give rise to mixtures of stereoisomers, these isomers may be separated by conventional techniques such as preparative chromatography. The compounds may be prepared in racemic form, or individual enantiomers may be prepared either by enantiospecific synthesis or by resolution. The compounds may, for example, be resolved into their component enantiomers by standard techniques, such as the formation of diastereomeric pairs by salt formation with an optically active acid, such as (−)-di-p-toluoyl-d-tartaric acid and/or (+)-di-p-toluoyl-l-tartaric acid followed by fractional crystallization and regeneration of the free base. The compounds may also be resolved by formation of diastereomeric esters or amides, followed by chromatographic separation and removal of the chiral auxiliary. Alternatively, the compounds may be resolved using a chiral HPLC column.

During any of the processes for preparation of the compounds of the present invention, it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene & P. G. M. Wuts, *Protective Groups in Organic Synthesis*, John Wiley & Sons, 1991. The protecting groups may be removed at a convenient subsequent stage using methods known from the art.

Abbreviations used in the instant specification, particularly the Schemes and Examples, are as follows:

Ar=aryl
CDI=1,1'-carbodiimidazole
DMF=dimethylformamide
Et=ethyl
EtOAc=ethyl acetate
EtOH=ethanol
HPLC=high pressure liquid chromatography
IPA or i-PrOH=isopropanol
i-Pr$_2$NEt=diisopropylethylamine
Me=methyl
MeOH=methanol
NMR=nuclear magnetic resonance
Ph=phenyl
TFA=trifluoroacetic acid
THF=tetrahydrofuran
TLC=thin layer chromatography Specific compounds useful according to the instant disclosure may be prepared according to the following synthesis scheme:

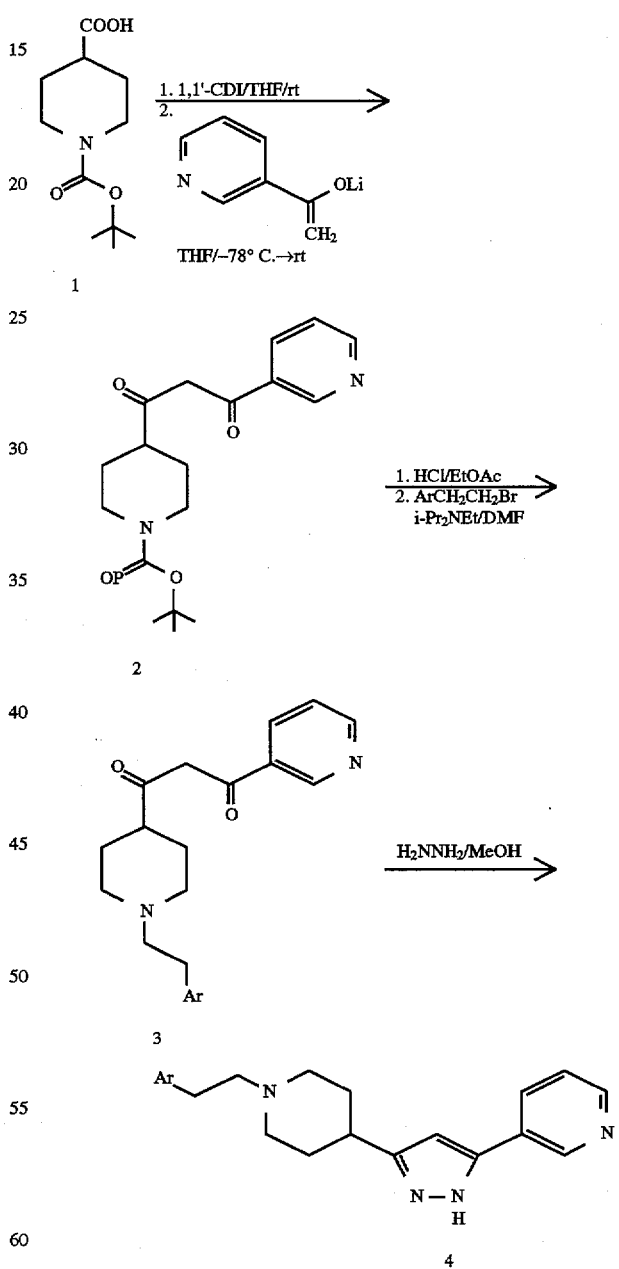

These compounds are administered in dosages effective to antagonize the alpha1a receptor where such treatment is needed, as in BPH. For use in medicine, the salts of the compounds of this invention (i.e., the compounds of formulas I and II above) refer to non-toxic "pharmaceutically acceptable salts." Other salts may, however, be useful in the preparation of the compounds according to the invention or of their pharmaceutically acceptable salts. Suitable pharmaceutically acceptable salts of the compounds of this invention include acid addition salts which may, for example, be formed by mixing a solution of the compound according to the invention with a solution of a pharmaceutically acceptable acid such as hydrochloric acid, sulphuric acid, fumaric acid, maleic acid, succinic acid, acetic acid, benzoic acid, oxalic acid, citric acid, tartaric acid, carbonic acid or phosphoric acid. Furthermore, where the compounds of the invention carry an acidic moiety, suitable pharmaceutically acceptable salts thereof may include alkali metal salts, e.g. sodium or potassium salts; alkaline earth metal salts, e.g. calcium or magnesium salts; and salts formed with suitable organic ligands, e.g. quaternary ammonium salts. Thus, representative pharmaceutically acceptable salts include the following:

Acetate, Benzenesulfonate, Benzoate, Bicarbonate, Bisulfate, Bitartrate, Borate, Bromide, Calcium, Camsylate, Carbonate, Chloride, Clavulanate, Citrate, Dihydrochloride, Edetate, Edisylate, Estolate, Esylate, Fumarate, Gluceptate, Gluconate, Glutamate, Glycollylarsanilate, Hexylresorcinate, Hydrabamine, Hydrobromide, Hydrochloride, Hydroxynaphthoate, Iodide, Isothionate, Lactate, Lactobionate, Laurate, Malate, Maleate, Mandelate, Mesylate, Methylbromide, Methylnitrate, Methylsulfate, Mucate, Napsylate, Nitrate, N-methylglucamine ammonium salt, Oleate, Oxalate, Pamoate (Embonate), Palmitate, Pantothenate, Phosphate/diphosphate, Polygalacturonate, Salicylate, Stearate, Sulfate, Subacetate, Succinate, Tannate, Tartrate, Teoclate, Tosylate, Triethiodide and Valerate.

The present invention includes within its scope prodrugs of s the compounds of this invention. In general, such prodrugs will be functional derivatives of the compounds of this invention which are readily convertible in vivo into the required compound. Conventional procedures for the selection and preparation of suitable prodrug derivatives are described, for example, in "Design of Prodrugs," ed. H. Bundgaard, Elsevier, 1985. Metabolites of these compounds include active species produced upon introduction of compounds of this invention into the biological mileu.

Where the compounds according to the invention have at least one chiral center, they may accordingly exist as enantiomers. Where the compounds according to the invention possess two or more chiral centers, they may additionally exist as diastereoisomers. It is to be understood that all such isomers and mixtures thereof are encompassed within the scope of the present invention. Furthermore, some of the crystalline forms for compounds of the present invention may exist as polymorphs and as such are intended to be included in the present invention. In addition, some of the compounds of the present invention may form solvates with water or common organic solvents. Such solvates are also encompassed within the scope of this invention.

The term "subject," as used herein refers to an animal, preferably a mammal, most preferably a human, who has been the object of treatment, observation or experiment.

The present invention also provides pharmaceutical compositions comprising one or more compounds of this invention in association with a pharmaceutically acceptable carrier. Preferably these compositions are in unit dosage forms such as tablets, pills, capsules, powders, granules, sterile parenteral solutions or suspensions, metered aerosol or liquid sprays, drops, ampoules, auto-injector devices or suppositories; for oral, parenteral, intranasal, sublingual or rectal administration, or for administration by inhalation or insufflation. Alternatively, the compositions may be presented in a form suitable for once-weekly or once-monthly administration; for example, an insoluble salt of the active compound, such as the decanoate salt, may be adapted to provide a depot preparation for intramuscular injection. For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation composition is then subdivided into unit dosage forms of the type described above containing from 0.1 to about 500 mg of the active ingredient of the present invention. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

The liquid forms in which the novel compositions of the present invention may be incorporated for administration orally or by injection include aqueous solutions, suitably flavoured syrups, aqueous or oil suspensions, and flavoured emulsions with edible oils such as cottonseed oil, sesame oil, coconut oil or peanut oil, as well as elixirs and similar pharmaceutical vehicles. Suitable dispersing or suspending agents for aqueous suspensions include synthetic and natural gums such as tragacanth, acacia, alginate, dextran, sodium carboxymethylcellulose, methylcellulose, polyvinylpyrrolidone or gelatin.

The specificity of binding of compounds showing affinity for the $\alpha 1a$ receptor is shown by comparing affinity to membranes obtained from tranfected cell lines that express the $\alpha 1a$ receptor and membranes from cell lines or tissues known to express other types of alpha (e.g., $\alpha 1d$, $\alpha 1b$) or beta adrenergic receptors. Expression of the cloned human $\alpha 1d$, $\alpha 1b$, and $\alpha 1a$ receptors and comparison of their binding properties with known selective antagonists provides a rational way for selection of compounds and discovery of new compounds with predictable pharmacological activities. Antagonism by these compounds of the human alpha1a adrenergic receptor subtype may be functionally demonstrated in anesthetized animals. These compounds may be used to increase urine flow without exhibiting orthostatic hypotensive effects.

The ability of compounds of the present invention to specifically bind to the $\alpha 1a$ receptor makes them useful for the treatment of BPH. The specificity of binding of compounds showing affinity for the $\alpha 1a$ receptor is compared against the binding affinities to other types of alpha or beta adrenergic receptors. The human alpha adrenergic receptor of the 1-a subtype was recently identified, cloned and expressed as described in PCT International Application Publication Nos. WO94/08040, published 14 Apr. 1994 and WO 94/21660, published 29 Sep. 1994, each of which is hereby incorporated by reference. The cloned human α1a receptor, when expressed in mammalian cell lines, is used to discover ligands that bind to the receptor and alter its function. Expression of the cloned human α1d, α1b, and α1a receptors and comparison of their binding properties with known selective antagonists provides a rational way for selection of compounds and discovery of new compounds with predictable pharmacological activities.

Compounds of this invention exhibiting selective human α1a adrenergic receptor antagonism may further be defined by counterscreening. This is accomplished according to methods known in the art using other receptors responsible for mediating diverse biological functions. [See e.g., PCT International Application Publication No. WO94/10989, published 26 May 1994]. Compounds which are both selective amongst the various human alpha1 adrenergic receptor subtypes and which have low affinity for other receptors, such as the alpha2 adrenergic receptors, the β-adrenergic receptors, the muscarinic receptors, the serotonin receptors, and others are particularly preferred. The absence of these non-specific activities may be confirmed by using cloned and expressed receptors in an analogous fashion to the method disclosed herein for identifying compounds which have high affinity for the various human alpha1 adrenergic receptors. Furthermore, functional biological tests are used to confirm the effects of identified compounds as alpha1a adrenergic receptor antagonists.

The present invention also has the objective of providing suitable topical, oral, systemic and parenteral pharmaceutical formulations for use in the novel methods of treatment of the present invention. The compositions containing compounds of this invention as the active ingredient for use in the specific antagonism of human alpha1a adrenergic receptors can be administered in a wide variety of therapeutic dosage forms in conventional vehicles for systemic administration. For example, the compounds can be administered in such oral dosage forms as tablets, capsules (each including timed release and sustained release formulations), pills, powders, granules, elixirs, tinctures, solutions, suspensions, syrups and emulsions, or by injection. Likewise, they may also be administered in intravenous (both bolus and infusion), intraperitoneal, subcutaneous, topical with or without occlusion, or intramuscular form, all using forms well known to those of ordinary skill in the pharmaceutical arts. An effective but non-toxic amount of the compound desired can be employed as an alpha1a antagonistic agent.

The term "therapeutically effective amount" as used herein means that amount of active compound or pharmaceutical agent that elicits the biological or medicinal response in a tissue, system, animal or human that is being sought by a researcher, veterinarian, medical doctor or other clinician, which includes alleviation of the symptoms of the disease being treated.

Advantageously, compounds of the present invention may be administered in a single daily dose, or the total daily dosage may be administered in divided doses of two, three or four times daily. Furthermore, compounds for the present invention can be administered in intranasal form via topical use of suitable intranasal vehicles, or via transdermal routes, using those forms of transdermal skin patches well known to those of ordinary skill in that art. To be administered in the form of a transdermal delivery system, the dosage administration will, of course, be continuous rather than intermittent throughout the dosage regimen.

The dosage regimen utilizing the compounds of the present invention is selected in accordance with a variety of factors including type, species, age, weight, sex and medical condition of the patient; the severity of the condition to be treated; the route of administration; the renal and hepatic function of the patient; and the particular compound thereof employed. A physician or veterinarian of ordinary skill can readily determine and prescribe the effective amount of the drug required to prevent, counter or arrest the progress of the condition. Optimal precision in achieving concentration of drug within the range that yields efficacy without toxicity requires a regimen based on the kinetics of the drug's availability to target sites. This involves a consideration of the distribution, equilibrium, and elimination of a drug.

In the methods of the present invention, the compounds herein described in detail can form the active ingredient, and are typically administered in admixture with suitable pharmaceutical diluents, excipients or carriers (collectively referred to herein as "carrier" materials) suitably selected with respect to the intended form of administration, that is, oral tablets, capsules, elixirs, syrups and the like, and consistent with conventional pharmaceutical practices.

For instance, for oral administration in the form of a tablet or capsule, the active drug component can be combined with an oral, non-toxic pharmaceutically acceptable inert carrier such as ethanol, glycerol, water and the like. Moreover, when desired or necessary, suitable binders, lubricants, disintegrating agents and coloring agents can also be incorporated into the mixture. Suitable binders include, without limitation, starch, gelatin, natural sugars such as glucose or beta-lactose, corn sweeteners, natural and synthetic gums such as acacia, tragacanth or sodium alginate, carboxymethylcellulose, polyethylene glycol, waxes and the like. Lubricants used in these dosage forms include, without limitation, sodium oleate, sodium stearate, magnesium stearate, sodium benzoate, sodium acetate, sodium chloride and the like. Disintegrators include, without limitation, starch, methyl cellulose, agar, bentonite, xanthan gum and the like.

The liquid forms in suitably flavored suspending or dispersing agents such as the synthetic and natural gums, for example, tragacanth, acacia, methyl-cellulose and the like. Other dispersing agents which may be employed include glycerin and the like. For parenteral administration, sterile suspensions and solutions are desired. Isotonic preparations which generally contain suitable preservatives are employed when intravenous administration is desired.

The compounds of the present invention can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

Compounds of the present invention may also be delivered by the use of monoclonal antibodies as individual carriers to which the compound molecules are coupled. The compounds of the present invention may also be coupled with soluble polymers as targetable drug carriers. Such polymers can include polyvinyl-pyrrolidone, pyran copolymer, polyhydroxypropylmethacryl-amidephenol, polyhydroxy-ethylaspartamidephenol, or polyethyleneoxidepolylysine substituted with palmitoyl residues. Furthermore, the compounds of the present invention may be coupled to a class of biodegradable polymers useful in achieving controlled release of a drug, for example, polylactic acid, polyepsilon caprolactone, polyhydroxy butyric acid, polyorthoesters, polyacetals, polydihydropyrans, polycyanoacrylates and cross-linked or amphipathic block copolymers of hydrogels.

Compounds of this invention may be administered in any of the foregoing compositions and according to dosage regimens established in the art whenever specific blockade of the human alpha1a adrenergic receptor is required.

The daily dosage of the products may be varied over a wide range from 0.1 to 1,000 mg per adult human/per day. For oral administration, the compositions are preferably provided in the form of tablets containing 0.01, 0.05, 0.1, 0.5, 1.0, 2.5, 5.0, 10.0, 15.0, 25.0, 50.0 and 100 milligrams of the active ingredient for the symptomatic adjustment of the dosage to the patient to be treated. An effective amount of the drug is ordinarily supplied at a dosage level of from about 0.01 mg/kg to about 10 mg/kg of body weight per day. Preferably, the range is from about 0.01 mg/kg to 7 mg/kg of body weight per day. The compounds may be administered on a regimen of 1 to 4 times per day.

Compounds of this patent disclosure may be used alone at appropriate dosages defined by routine testing in order to obtain optimal antagonism of the human $\alpha 1a$ adrenergic receptor while minimizing any potential toxicity. In addition, co-administration or sequential administration of other agents which alleviate the effects of BPH is desirable. Thus, in one embodiment, this includes administration of compounds of this invention and a human testosterone 5-$\alpha$ reductase inhibitor. Included with this embodiment are inhibitors of 5-alpha reductase isoenzyme 2. Many such compounds are now well known in the art and include such compounds as PROSCAR®, (also known as finasteride, a 4-Aza-steroid; see U.S. Pat. Nos. 4,377,584 and 4,760,071, for example, hereby incorporated by reference). In addition to PROSCAR®, which is principally active in prostatic tissue due to its selectivity for human 5-$\alpha$ reductase isozyme 2, combinations of compounds which are specifically active in inhibiting testosterone 5-alpha reductase isozyme 1and compounds which act as dual inhibitors of both isozymes 1and 2, are useful in combination with compounds of this invention. Compounds that are active as 5$\alpha$-reductase inhibitors have been described in WO93/23420, EP 0572166; WO 93/23050; WO93/23038, ;WO93/23048; WO93/23041; WO93/23040; WO93/23039; WO93/23376; WO93/23419, EP 0572165; WO93/23051, each of which is hereby incorporated by reference.

The dosages of the alpha1a adrenergic receptor and testosterone 5-alpha reductase inhibitors are adjusted when combined to achieve desired effects. As those skilled in the art will appreciate, dosages of the 5-alpha reductase inhibitor and the alpha1a adrenergic receptor may be independently optimized and combined to achieve a synergistic result wherein the pathology is reduced more than it would be if either agent were used alone. In accordance with the method of the present invention, the individual components of the combination can be administered separately at different times during the course of therapy or concurrently in divided or single combination forms. The instant invention is therefore to be understood as embracing all such regimes of simultaneous or alternating treatment and the term "administering" is to be interpreted accordingly.

Thus, in one preferred embodiment of the present invention, a method of treating BPH is provided which comprises administering to a subject in need of treatment any of the compounds of the present invention in combination with finasteride effective to treat BPH. The dosage of finasteride administered to the subject is about 0.01 mg per subject per day to about 50 mg per subject per day in combination with an $\alpha 1a$ antagonist. Preferably, the dosage of finasteride used in the combination is about 0.2 mg per subject per day to about 10 mg per subject per day, more preferably, about 1 to about 7 mg per subject to day, most preferably, about 5 mg per subject per day.

For the treatment of benign prostatic hyperplasia, compounds of this invention exhibiting alpha1a adrenergic receptor blockade can be combined with a therapeutically effective mount of a 5$\alpha$-reductase 2 inhibitor, such as finasteride, in addition to a 5$\alpha$-reductase 1 inhibitor, such as 4,7$\beta$-dimethyl-4-aza-5$\alpha$-cholestan-3-one, in a single oral, systemic, or parenteral pharmaceutical dosage formulation. Alternatively, a combined therapy can be employed wherein the alpha1a adrenergic receptor antagonist and the 5$\alpha$-reductase 1 or 2 inhibitor are administered in separate oral, systemic, or parenteral dosage formulations. See, e.g., U.S. Pat. Nos. 4,377,584 and 4,760,071 which describe dosages and formulations for 5$\alpha$-reductase inhibitors.

The following examples are provided to further define the invention without, however, limiting the invention to the particulars of these examples. All NMRs were run on a 400 mHz instrument.

EXAMPLE 1

1-(2-(1-Naphthyl)ethyl)-4-(5-(pyridin-3-yl)pyrazol-3-yl)piperidine

Step A: 1-(1,1-Dimethylethoxycarbonyl)-4-(1-(3-hydroxy-1-oxo -3-(3-pyridinyl)-2-propenyl)piperidine To an oven dried 50 mL round bottomed flask with a stirring bar, argon inlet and septum was added Boc-isonipecotic acid (2.50 g, 10.90 mmol), 1,1'-carbonyldiimidazole (1.77 g, 10.90 mmol) and dry THF (20 mL). This solution was stirred at 20° C. for 45 min. To a separate, oven dried, 100 mL round bottomed flask with a stirring bar, argon inlet, low temperature thermometer, and septum was added dry THF (30 mL) and distilled diisopropylamine (1.60 mL, 11.45 mmol). This solution was cooled to −78° C. and n-Butyllithium (4.58 mL, of a 2.5M solution in hexane, 11.45 mmol) was added with a syringe. This solution was aged 20 min. then 3-acetylpyridine (1.25 mL, 11.45 mmol) was added dropwise with a syringe. This mixture was stirred for 30 min. at −78° C. then the imidazolide solution was added via a cannula. The mixture was warmed to 20° C. then diluted with EtOAc (350 mL). This solution was washed with 10% aqueous citric acid, saturated aqueous NaHCO$_3$ solution and brine. Drying (MgSO$_4$), filtration and removal of the solvent in vacuo gave an oil. This material was chromatographed on 120 g of silica gel using 3% 2-propanol in CHCl$_3$ as eluant. 1-(1,1-dimethylethoxycarbonyl)-4-(1-(3-hydroxy-1-oxo-3-(3-pyridinyl)-2-propenyl)piperidine was obtained as an oil.

Step B: 4-(1-(3-Hydroxy-1-oxo-3-(3-pyridinyl)-2-propenyl) piperidine dihydrochloride To a 500 mL round bottomed flask with a stirring bar and a sparging tube was added 1-(1,1-dimethylethoxycarbonyl)-4-(1-(3-hydroxy-1-oxo-3-(3-pyridinyl)-2-propenyl) piperidine (3.08 g, 9.27 mmol) and dry EtOAc (250 mL). This solution was cooled in an ice bath and dry HCl gas was bubbled through the mixture vigorously for 5 min. The mixture was stirred an additional 30 min. at 0° C. then the excess HCl was removed with argon gas. The solvent was removed in vacuo and the solid was recrystallized from MeOH/Et$_2$O to give 4-(1-(3-hydroxy-1-oxo-3-(3-pyridinyl)-2-propenyl)piperidine dihydrochloride.

Step C: 1-(2-(1-Naphthyl)ethyl)-4-(1-(3-hydroxy-1-oxo-3-(3-pyridinyl)-2-propenyl)piperidine To 10 mL round bottomed flask with a stirring bar and an argon inlet was added 4-(1-(3-hydroxy-1-oxo-3-(3- pyridinyl)-2-propenyl)piperidine dihydrochloride (400mg, 1.31 mmol), 1-(2-bromoethyl)naphthalene (616 mg, 2.62 mmol) dry DMF (5 mL), and diisopropylethylamine (1.74 mL, 10 mmol). This mixture was heated at 60° C. for 24 h. The DMF was removed in vacuo and the residue was dissolved in EtOAc. This solution was washed with saturated aqueous $NaHCO_3$, $H_2O$ and brine. Drying ($Na_2SO_4$), filtration and removal of the solvent in vacuo gave an orange oil. This material was chromatographed on 30 g of silica gel using 5% 2-propanol in $NH_3$ saturated $CHCl_3$ as eluant. 1-(2-(1-naphthyl)ethyl)-4-(1-(3-hydroxy-1-oxo-3-(3-pyridinyl)-2-propenyl)piperidine was obtained as a white solid.

Step D: 1-(2-(1-Naphthyl)ethyl)-4-(5-(pyridin-3-yl)pyrazol-3-yl)piperidine

To a 50 mL round bottomed flask with a stirring bar and an argon inlet was added 1-(2-(1-naphthyl)ethyl)-4-(1-(3-hydroxy-1-oxo-3-(3-pyridinyl)-2-propenyl)piperidine (252 mg, 0.65 mmol), $CH_3OH$ (10 mL) and anhydrous hydrazine (0.1 mL, 3.20 mmol). This mixture was stirred at 20° C. for 2.5 h. The solvent was removed in vacuo and the residue was chromatographed on 30 g of silica gel using 4% 2-propanol in $NH_3$ saturated $CHCl_3$ as eluant. The chromatographed material was recrystallized from EtOAc-hexane to give 1-(2-(1-naphthyl)ethyl)-4-(5-(pyridin-3-yl)pyrazol-3-yl) piperidine, mp: 171°–173° C.

$^1$H NMR ($CDCl_3$): d 1.90 (m, 2H); 2.06 (m, 2H); 2.22 (m, 2H); 2.75 (m, 2H), 3.21 (br d, J=12 Hz, 2H); 3.31 (m, 2H); 6.46 (s, 1H); 7.30–7.55 (m, 5H); 7.72 (d, J=8 Hz, 1H); 7.85 (d, J=8 Hz, 1H); 8.80 (d, J=8 Hz, 2H); 8.56 (dd, J=2,5 Hz, 1H); 9.02 (d, J=2 Hz, 1H); 9.02 (br s, 1H).

EXAMPLE 2

1-(2-(3-Indolyl)ethyl)-4-(5-(pyridin-3-yl)pyrazol-3-yl)piperdine

In a manner similar to that described for EXAMPLE 1 but substituting 3-(2-bromoethyl)indole for 1-(2-bromoethyl) naphthalene in Step C, 1-(2-(3-indolyl)ethyl)-4-(5-(pyridin-3-yl)pyrazol-3-yl)piperdine was prepared. The dihydrochloride salt was prepared from 2-propanol/HCl, mp: 200° C. (dec).

$^1$H NMR ($CDCl_3$): d 1.90 (m, 2H); 2.06 (m, 2H); 2.22 (m, 2H); 2.75 (m, 2H), 3.21 (br d, J=12 Hz, 2H); 3.31 (m, 2H); 6.41 (s, 1H); 7.10 (d, J=1.8 Hz, 1H); 7.12 (t, J=7 Hz, 1H); 7.19 (t, J=7 Hz, 1H); 7.35 (m, 2H); 7.62 (d, J=11 Hz, 1H); 8.04 (br d, J=6 Hz, 1H); 8.14 (br s, 1H); 8.56 (dd, J=2,8 Hz, 1H); 9.01 (br s, 1H); 10.80 (br s, 1H).

EXAMPLE 3

1-(2-(1-Naphthyl)ethyl)-4-(5-(3,4-dichlorophenyl)pyrazol-3-yl)piperdine

In a manner similar to that described for EXAMPLE 1 but substituting 3,4-dichloroacetophenone for 3-acetylpyridine in Step A, 1-(2-(1-naphthyl)ethyl)-4-(5-(3,4-dichlorophenyl)pyrazol-3-yl)piperdine was prepared, mp: 144°–146° C.

$^1$H NMR ($CDCl_3$): d 1.87 (m, 2H); 2.03 (m, 2H); .2.21 (m, 2H); 2.75 (m, 2H); 3.20 (br d, 11 Hz, 2H); 3.30 (m, 2H); 6.39 (s, 1H); 7.37 (br m, 6H); 7.72 (d, J=8 Hz, 1H); 7.86 (br s, 2H); 8.05 (d, J=8 Hz, 1H) 10.6 (br s, 1H).

EXAMPLE 4

1-(2-(1-Naphthyl)ethyl)-4-(5-(3,4-dimethoxyphenyl)pyrazol-3-yl)piperdine

In a manner similar to that described for EXAMPLE 1 but substituting 3,4-dimethoxyacetophenone for 3-acetylpyridine in Step A, 1-(2-(1-naphthyl)ethyl)-4-(5-(3,4-dimethoxyphenyl)pyrazol-3-yl)piperdine was prepared, mp: 117°–119° C.

$^1$H NMR ($CDCl_3$): d 1.89 (m, 2H); 2.06 (br d, J=12 Hz, 2H); 2.22 (t, J=11 Hz, 2H); 2.73 (m, 3H); 3.20 (br d, J=11 Hz, 2H); 3.31 (m, 2H); 3.92 (s, 3H); 3.96 (s, 3H); 6.36 (s, 1H); 6.91 (d, J=8.4 Hz, 1H); 7.37 (m, 3H); 7.40 (m, 3H); 7.73 (d, J=7.9 Hz, 1H); 7.86 (d, J=8.2 Hz, 1H); 8.07 (d, J=8.2 Hz, 1H); 9.70 (br s, 1H).

EXAMPLE 5

1-(2-(1-Naphthyl)ethyl)-4-(5-(3-nitrophenyl)pyrazol-3-yl)piperdine

In a manner similar to that described for EXAMPLE 1 but substituting 3-nitroacetophenone for 3-acetylpyridine in Step A, 1-(2-(1-naphthyl)ethyl)-4-(5-(3-nitrophenyl)pyrazol-3-yl)piperdine was prepared, mp: 158°–160° C.

1H NMR ($CDCl_3$): d 1.90 (m, 2H); 2.04 (m, 2H); 2.26 (m, 2H); 2.76 (m, 3H); 3.21 (d, J=4.0 Hz, 2H); 3.31 (m, 2H); 6.51 (s, 1H); 7.36 (m, 2H); 7.41 (m, 3H); 7.73 (d, J=8.0 Hz, 1H); 7.86 (d, J=7.7 Hz, 1H); 8.06 (d, J=8.2 Hz, 2H); 8.12 (m, 2H); 8.61 (s, 1H); 10.0 (br s, 1H).

EXAMPLE 6

1-(2-Phenylethyl)-4-(5-(3-nitrophenyl)pyrazol-3-yl)piperdine

In a manner similar to that described for EXAMPLE 5 but substituting 2-phenethylbromide for 1-(2-bromoethyl) naphthalene in Step C, 1-(2-(phenyl)ethyl)-4-(5-(3-nitrophenyl)pyrazol-3-yl)piperdine was prepared, mp: 155°–156° C.

$^1$H NMR ($CDCl_3$): d 1.84 (m, 2H); 2.03 (m, 2H); 2.15 (m, 2H); 2.63 (m, 2H); 2.75 (m, 1H); 2.83 (m, 2H); 3.11 (d, J=10 Hz, 2H); 6.49 (s, 1H); 7.20 (m, 5H); 7.55 (t, J=8 Hz, 1 H); 8.11 (m, 2H); 8.60 (s, 1H); 10.3 (br s, 1H).

EXAMPLE 7

1-(2-(1-Naphthyl)ethyl)-4-(5-(3-bromophenyl)pyrazol-3-yl)piperdine

In a manner similar to that described for EXAMPLE 1 but substituting 3-bromoacetophenone for 3-acetylpyridine in Step A, 1-(2-(1-naphthyl)ethyl)-4-(5-(3-bromophenyl)pyrazol-3-yl)piperdine was prepared, mp: 108°–110° C.

1H NMR ($CDCl_3$): d 1.87(m, 2H); 2.05 (d, J=11.9 Hz, 2H); 2.21 (m, 2H); 2.72 (m, 3H); 3.19 (d, J=11.6 Hz, 2H); 3.30 (m, 2H); 6.40 (s, 1H); 7.27 (d, J=7.9 Hz, 1H); 7.36 (m, 5H); 7.67 (d, J=6.0 Hz, 1H); 7.72 (d, J=7.9 Hz, 1H); 7.85 (dd, J=7.3, 1.3 Hz, 1H); 7.91 (s, 1H); 8.06 (d, J=8.2 Hz, 1H); 9.95 (br s, 1H).

EXAMPLE 8

1-(2-Phenylethyl)-4-(5-(3-bromophenyl)pyrazol-3-yl)piperdine

In a manner similar to that described for EXAMPLE 7 but substituting 2-phenethylbromide for 2-(1-naphthyl) ethylbromide in Step C, 1-(2-(phenyl)ethyl)-4-(5-(3-bromophenyl)pyrazol-3-yl)piperdine was prepared, mp: 124°–125° C.

1H NMR ($CDCl_3$): d 1.82 (m, 2H); 2.01 (m, 2H); 2.15 (m, 2H); 2.62 (m, 2H); 2.70 (m, 1H); 2.82 (m, 2H); 3.10 (d, J=11 Hz, 2H); 6.38 (s, 1H); 7.21 (m, 5H); 7.43 (d, J=8 Hz, 1H); 7.66 (br s, 1H); 7.90 (br s, 1H); 10.8 (br s, 1H).

EXAMPLE 9

1-(2-(1-Naphthyl)ethyl)-4-(5-(3-cyanophenyl)pyrazol-3-yl)piperdine

In a manner similar to that described for EXAMPLE 1 but substituting 3-cyanoacetophenone for 3-acetylpyridine in Step A, 1-(2-(1-naphthyl)ethyl)-4-(5-(3-cyanophenyl)pyrazol-3-yl)piperdine was prepared, mp: 135°–137° C.

1H NMR (CDCl$_3$): d 1.85 (m, 2H); 2.05 (d, J=11.4 Hz, 2H); 2.22 (br t, J=11.5 Hz, 2H); 2.74 (m, 3H); 3.20 (d, J=11.2 Hz, 2H); 3.30 (m, 2H); 6.43 (s, 1H); 7.36 (m, 5H); 7.58 (d, J=7.7 Hz, 1H); 7.72 (d J=8.0 Hz, 1H); 7.85 (d, J=7.2 Hz, 1 H); 8.0 (d, J=7.7 Hz 1H); 8.06 (d, J=7.5 Hz, 1H); 9.99 (br s, 1H).

EXAMPLE 10

1-(2-Phenylethyl)-4-(5-(3-cyanophenyl)pyrazol-3-yl)piperdine

In a manner similar to that described for EXAMPLE 9 but substituting 2-phenethylbromide for 2-(1-naphthyl)ethylbromide in Step C, 1-(2-(phenyl)ethyl)-4-(5-(3-cyanophenyl)pyrazol-3-yl)piperdine was prepared, mp: 148°–150° C.

$^1$H NMR (CDCl$_3$): d 1.83 (m, 2H); 2.02 (m, 2H); 2.14 (t, J=11 Hz, 2H); 2.63 (m, 2H); 2.67 (m, 1H); 2.84 (m, 2H); 3.11 (d, J=11 Hz, 2 H); 7.20 (m, 5H); 7.48 (m, 1H); 7.57 (d, J=7 Hz, 1H); 8.01 (br m, 2H); 10.0 (br s, 1H).

EXAMPLE 11

1-(2-(1-Naphthyl)ethyl)-4-(5-(4-cyanophenyl)pyrazol-3-yl)piperdine

In a manner similar to that described for EXAMPLE 1 but substituting 4-cyanoacetophenone for 3-acetylpyridine in Step A, 1-(2-(1-naphthyl)ethyl)-4-(5-(4-cyanophenyl)pyrazol-3-yl)piperdine was prepared, mp: 229°–230° C.

1H NMR (CDCl$_3$): d 1.89 (m, 2H); 2.03 (m, 2H); 2.25 (br t, J=11.5 Hz, 2H), 2.78 (m, 3H); 3.20 (br d, J=12 Hz, 2H); 3.26 (m, 2H); 6.47 (s, 1H); 7.36 (m, 2H); 7.52 (m, 2H); 7.71 (m, 3H); 7.86 (m, 3H); 8.06 (d, J=8.4 Hz, 1H); 9.98 (br s, 1H).

EXAMPLE 12

1-(2-(1-Naphthyl)ethyl)-4-(5-(2-pyridyl)pyrazol-3-yl)piperdine

In a manner similar to that described for EXAMPLE 1 but substituting 2-acetylpyridine for 3-acetylpyridine in Step A, 1-(2-(1-naphthyl)ethyl)-4-(5-(2-pyridyl)pyrazol-3-yl)piperdine was prepared, mp: 154°–155° C.

$^1$H NMR (CDCl$_3$): d 1.94 (m, 2H); 2.04 (m, 2H); 2.26 (br t, J=11 Hz, 2H); 2.78 (m, 3H); 3.20 (br d, J=11 Hz, 2H); 3.34 (br t, J=8.5 Hz, 2H); 6.23 (s, 1H); 7.21 (m, 1H); 7.40 (m, 2H); 7.49 (m, 2H); 7.72 (m, 2H); 7.84 (d, J=8 Hz, 1H); 8.09 (d, J=8 Hz, 1H); 8.61 (d, J=4.5 Hz, 1H); 11.03 (br s, 1H).

EXAMPLE 13

1-(2-(1-Naphthyl)ethyl)-4-(5-(2-naphthyl)pyrazol-3-yl)piperdine

In a manner similar to that described for EXAMPLE 1 but substituting 2-acetylnaphthalene for 3-acetylpyridine in Step A, 1-(2-(1-naphthyl)ethyl)-4-(5-(2-naphthyl)pyrazol-3-yl)piperdine was prepared, mp: 180°–182° C.

$^1$H NMR (CDCl$_3$): d 1.91 (m, 2H); 2.09 (m, 2H); 2.23 (br t, J=11.7 Hz, 2H); 2.77 (m, 3H); 3.21 (br d, J=11.5 Hz, 2H); 3.31 (m, 2H); 6.55 (s, 1H); 7.37 (m, 2H); 7.47 (m, 4H); 7.72 (d, J=7.7 Hz, 1H); 7.82 (m, 6H); 8.0 (d, J=8 Hz, 1H); 9.82 (br s, 1H).

EXAMPLE 14

1-(2-(1-Naphthyl)ethyl)-4-(5-(benzodioxan-6-yl)pyrazol-3-yl)piperdine

In a manner similar to that described for EXAMPLE 1 but substituting 6-acetylbenzodioxane for 3-acetylpyridine in Step A, 1-(2-(1-naphthyl)ethyl)-4-(5-(benzodioxan-6-yl)pyrazol-3-yl)piperdine was prepared, mp: 185°–187° C.

$^1$H NMR (CDCl$_3$): d 1.86 (m, 2H); 2.04 (m, 2H); 2.24 (m, 2H); 2.74 (m, 3H); 3.18 (d, J=11 Hz, 2H); 3.30 (m, 2H); 4.28 (s, 4H); 6.31 (s, 1H); 6.90 (d, J=8 Hz, 1H); 7.36 (m, 2H); 7.42 (m, 2H); 7.20 (d, J=8 Hz, 1H); 7.85 (d, J=8 Hz, 1H); 8.06 (d, J=8 Hz, 1H); 9.80 (br s, 1H).

EXAMPLE 15

1-(2-(1-Naphthyl)ethyl)-4-(5-(2-furyl)pyrazol-3-yl)piperdine

In a manner similar to that described for EXAMPLE 1 but substituting 2-acetylfuran for 3-acetylpyridine in Step A, 1-(2-(1-naphthyl)ethyl)-4-(5-(2-furyl)pyrazol-3-yl)piperdine was prepared, mp: 122°–123° C.

$^1$H NMR (CDCl$_3$): d 1.87 (m, 2H); 2.04 (br d, J=12.9 Hz, 2H); 2.21 (br t, J=11 Hz, 2H); 2.72 (m, 3H), 3.18 (d, J=10.5 Hz, 2H); 3.30 (t, J=8 Hz, 2H); 6.35 (s, 1H); 6.46 (d, J=1.8 Hz, 1H); 6.62 (d, J=3.0 Hz, 1H); 7.36 (m, 5H); 7.72 (d, J=7.9 Hz, 1H); 7.85 (d, J=8.2 Hz, 1H); 8.06 (d, J=8.2 Hz, 1H); 9.84 (br s, 1H).

EXAMPLE 16

1-(2-(1-Naphthyl)ethyl)-4-(5-(3-thienyl)pyrazol-3-yl)piperdine

In a manner similar to that described for EXAMPLE 1 but substituting 3-acetylthiophene for 3-acetylpyridine in Step A, 1-(2-(1-naphthyl)ethyl)-4-(5-(3-thienyl)-3-yl)piperdine was prepared, mp: 124°–125° C.

$^1$H NMR (CDCl$_3$): d 1.88 (m, 2H); 2.04 (br d, J=12.6 Hz, 2H); 2.21 (t, J=11.5 Hz, 2H); 2.71 (m, 3H); 3.18 (d, J=11.4 Hz, 2H); 3.30 (m, 2H); 6.31 (s, 1H); 7.40 (m, 4H); 7.46 (m, 3H); 7.72 (d, J=7.7 Hz, 1H); 7.85 (d, J=7.4 Hz, 1H); 8.06 (d, J=8.0 Hz, 1H); 9.82 (br s, 1H).

EXAMPLE 17

1-(2-(1-Naphthyl)ethyl)-4-(5-(3,4-methylenedioxyphenyl)pyrazol-3-yl)piperdine

In a manner similar to that described for EXAMPLE 1 but substituting 3,4-methylenedioxyacetophenone for 3-acetylpyridine in Step A, 1-(2-(1-naphthyl)ethyl)-4-(5-(3,4-methylenedioxyhenyl)pyrazol-3-yl)piperdine was prepared, mp: 168°–170° C.

$^1$H NMR (CDCl$_3$): d 1.87 (m, 2H); 2.04 (d, J=11.7 Hz, 2H); 2.21 (t, J=11.5 Hz, 2H); 2.71 (m, 3H); 3.19 (d, J=11.2 Hz, 2H); 3.30 (m, 2H); 6.0 (s, 2H); 6.31 (s, 1H); 6.84 (d, J=7.9 Hz, 1H); 7.36 (m, 3H); 7.41 (m, 3H); 7.72 (d, J=7.7 Hz, 1H); 7.85 (d, J=7.7 Hz, 1H); 8.06 (d, J=8.4 Hz, 1H); 9.7 (br s, 1H).

EXAMPLE 18

1-(2-(1-Naphthyl)ethyl)-4-(5-(4-methoxyphenyl)pyrazol-3-yl)piperdine

In a manner similar to that described for EXAMPLE 1 but substituting 4-methoxyacetophenone for 3-acetylpyridine in Step A, 1-(2-(1-naphthyl)ethyl)-4-(5-(4-methoxyphenyl) pyrazol-3-yl)piperdine was prepared, mp: 141°–144° C.

$^1$H NMR (CDCl$_3$): d 1.88 (m, 2H); 2.04 (m, 2H); 2.21 (m, 2H); 2.75 (m, 3H); 3.19 (d, J=11 Hz, 2H); 3.30 (m, 2H); 3.84 (s, 3H); 6.34 (s, 1H); 6.93 (d, J=8.6 Hz, 2H); 7.35 (m, 3H); 7.47 (m, 3H); 7.72 (d, J=7.4 Hz, 1H); 7.85 (d, J=7.6 Hz, 1H); 8.06 (d, J=8 Hz, 1H), 9.95 (br s, 1H).

EXAMPLE 19

1-(2-(1-Naphthyl)ethyl)-4-(5-(6-quinolinyl)pyrazol-3-yl)piperdine

In a manner similar to that described for EXAMPLE 1 but substituting 6-acetylquinoline for 3-acetylpyridine in Step A, 1-(2-(1-naphthyl)ethyl)-4-(5-(6-quinolinyl)pyrazol-3-yl) piperdine was prepared, mp: 180°–182° C.

$^1$NMR (CDCl$_3$): d 1.91 (m, 2H); 2.09 (m, 2H); 2.23 (m, 2H); 2.75 (m, 3H); 3.21(d, J=11.7 Hz, 2H); 3.31 (m, 2H); 6.57 (s, 1H); 7.32 (m, 3H); 7.41 (m, 2H); 7.73 (d, J=7.4 Hz, 1 H); 7.86 (d, J=7.5 Hz, 1H); 8.07 (d, J=8 Hz, 1H); 8.13 (m, 4H); 8.90 (dd, J=4, 1.5 Hz, 1H); 10 (br s, 1H).

EXAMPLE 20

1-(2-(2,6-Dimethoxyphenoxy)ethyl)-4-(5-(pyridin-3-yl)pyrazol-3-yl)piperdine

In a manner similar to that described for EXAMPLE 1 but substituting 2-(2,6-dimethoxyphenoxy)ethylbromide for 1-(2-bromoethyl)naphthalene in Step C, 1-(2-(2,6-dimethoxyphenoxy)ethyl)-4-(5-(pyridin-3-yl)pyrazol-3-yl) piperdine was prepared, mp: 149°–151° C.

$^1$H NMR (CDCl$_3$): d 1.89 (m, 2H); 2.01 (br d, J=7.9 Hz, 2H); 2.23 (m, 2H); 2.73 (m, 1H); 2.83 (t, J=6.0 Hz, 2H); 3.19 (br d, J=11.8, 2H); 3.84 (s, 6H); 4.12 (t, J=6.0 Hz, 2H); 6.43 (s, 1H); 6.57 (d, J=1.6 Hz, 2H); 6.99 (t, J=8.4 Hz, 1H); 7.32 (m, 1H); 8.06 (br d, J=7.22 Hz, 1H); 8.55 (m, 1H); 9.00 (s, 1H); 10.08 (br s, 1H).

EXAMPLE 21

1-(2-(2-Ethoxyphenoxy)ethyl)-4-(5-(pyridin-3-yl) pyrazol-3-yl)piperdine

In a manner similar to that described for EXAMPLE 1 but substituting 2-(2-ethoxyphenoxy)ethylbromide for 1-(2-bromoethyl)naphthalene in Step C, 1-(2-(2-ethoxyphenoxy) ethyl)-4-(5-(pyridin-3-yl)pyrazol-3-yl)piperdine was prepared, mp: 104°°–105° C.

$^1$H NMR (CDCl$_3$): d 1.42 (m, 3H); 1.85 (m, 2H); 2.01 (br d, J=7.9 Hz, 2H); 2.29 (m, 2H); 2.73 (m, 1H); 2.89 (t, J=11.5 Hz, 2H); 3.15 (br d, J=11.5 Hz, 2H); 4.08 (m, 2H); 4.15 (m, 2H); 6.42 (2, 1H); 6.90 (m, 4H); 7.32 (m, 1H); 8.04 (br d, J=7.3, 1H); 8.55 (m, 1H); 8.99 (s, 1H); 9.99 (br s, 1H).

EXAMPLE 22

1-(2-(2-Methoxyphenyl)ethyl)-4-(5-(pyridin-3-yl) pyrazol-3-yl)piperdine

In a manner similar to that described for EXAMPLE 15 but substituting 2-(2-methoxyphenyl)ethylbromide for 1-(2-bromoethyl)naphthalene in Step C, 1-(2-(2-methoxyphenyl) ethyl)-4-(5-(pyridin-3-yl)pyrazol-3-yl)piperdine was prepared, mp: 132°–134° C.

$^1$H NMR (CDCl$_3$): d 2.00 (br m, 4H); 2.25 (br s, 2H); 2.60 (br m, 3H); 2.91 (br s, 2H); 3.21 (br s, 2H); 3.81 (s, 3H); 6.42 (s, 1H); 6.88 (m, 2H); 7.25 (m, 1H); 8.03 (d, J=7.5 Hz, 1H); 8.55 (dd, J=1.5, 5 Hz, 1H); 9.00 (s, 1H); 10.80 (br s, 1H).

EXAMPLE 23

1-(2-(2-Naphthyl)ethyl)-4-(5-(pyridin-3-yl)pyrazol-3-yl)piperdine

In a manner similar to that described for EXAMPLE 1 but substituting 2-(2-bromoethyl)naphthalene for 1-(2-bromoethyl)naphthalene in Step C, 1-(2-(2-naphthyl)ethyl) -4-(5-(pyridin-3-yl)pyrazol-3-yl)piperdine was prepared, mp: 190°–190.5° C.

$^1$H NMR (CDCl$_3$): d 1.88 (m, 2H); 2.05 (m, 2H); 2.21 (dt, J=2, 10 Hz, 2H); 2.75 (m, 3H); 3.01 (m, 2H); 3.17 (br d, J=11.6 Hz, 2H); 6.44 (s, 1H); 7.35 (m, 2H); 7.45 (m, 2H); 7.65 (s, 1H); 7.80 (m, 3H); 8.05 (br d, J=7.5 Hz, 1H); 8.55 (dd, J=1.5, 5 Hz, 1H); 9.00 (s, 1H); 10.20 (br s, 1H).

EXAMPLE 24

1-(2-(4-Methoxyphenyl)ethyl)-4-(5-(pyridin-3-yl) pyrazol-3-yl)piperdine

In a manner similar to that described for EXAMPLE 1 but substituting 2-(4-methoxyphenyl)ethylbromide for 1-(2-bromoethyl)naphthalene in Step C, 1-(2-(4-methoxyphenyl) ethyl)-4-(5-(pyridin-3-yl)pyrazol-3-yl)piperdine was prepared, mp: 184°–186° C.

$^1$H NMR (CDCl$_3$): d 1.86 (m, 2H); 2.03 (br d, J=11.4 Hz, 2H); 2.16 (m, 2H); 2.60 (m, 2H); 2.76 (m, 3H); 3.11 (br d, J=1 1.75 Hz, 2H); 3.79 (s, 3H); 6.44 (s, 1H); 6.84 (m, 2H); 7.13 (m, 2H); 7.33 (m, 1H); 8.06 (br d, J=6.7 Hz, 1H); 8.56 (m, 1H); 9.00 (s, 1H); 10.15 (br s, 1H).

EXAMPLE 25

1-(2-(3-Methoxyphenyl)ethyl)-4-(5-(pyridin-3-yl) pyrazol-3-yl)piperdine

In a manner similar to that described for EXAMPLE 1 but substituting 2-(3-methoxyphenyl)ethylbromide for 1-(2-bromoethyl)naphthalene in Step C, 1-(2-(3-methoxyphenyl) ethyl)-4-(5-(pyridin-3-yl)pyrazol-3-yl)piperdine was prepared, mp: 163°–165° C.

$^1$H NMR (CDCl$_3$): d 1.85 (m, 2H); 2.04 (br d, J=11.4 Hz, 2H); 2.17 (m, 2H); 2.65 (m, 2H); 2.79 (m, 3H); 3.11 (br d, J=11.04 Hz, 2H); 3.81 (s, 3H); 6.44(d, J=0.5 Hz, 1H); 6.78 (m, 3H); 7.22 (m, 1H); 7.31 (m, 1H); 8.05 (br d, J=7.89, 1H); 8.56 (m, 1H); 9.00 (d, J=1.68 Hz, 1H); 9.91 (br s, 1H).

EXAMPLE 26

1-(2-(Benzothiophen-3-yl)ethyl)-4-(5-(pyridin-3-yl) pyrazol-3-yl)piperdine

In a manner similar to that described for EXAMPLE 1 but substituting 3-(2-bromoethyl)benzothiophene for 1-(2-bromoethyl)naphthalene in Step C, 1-(2-(benzothiophen-3-yl)ethyl)-4-(5-(pyridin-3-yl)pyrazol-3-yl)piperdine was prepared, mp: 176°–177° C.

$^1$H NMR (CDCl$_3$): d 1.88 (m, 2H); 2.06 (br d, J=12.4 Hz, 2H); 2.22 (m, 2H); 2.79 (m, 3H); 3.09 (t, J=7.8, 2H); 3.17 (d, J=11.6 Hz, 2H); 6.46 (s, 1H); 7.19 (s, 1H); 7.37 (m, 3H); 7.78 (m, 1H); 7.87 (m, 1H); 8.06 (br d, J=8.2 Hz, 1H); 8.56 (m, 1H); 9.01 (d, J=1.51 Hz, 1H); 10.0 (br s, 1H).

EXAMPLE 27

1-(2-(N-benzimidazol-2-one)ethyl)-4-(5-(pyridin-3-yl)pyrazol-3-yl)piperdine

In a manner similar to that described for EXAMPLE 1 but substituting N-(2-bromoethyl)benzimidazol-2-one for 1-(2- bromoethyl)naphthalene in Step C, 1-(2-(benzimidazol-2-one)ethyl)-4-(5-(pyridin-3-yl)pyrazol-3-yl)piperdine was prepared, HCl salt, mp: 219°–223° C. (decomposed).

$^1$H NMR (CD$_3$OD): d 2.03 (bq, J=11.5 Hz, 2H), 2.38 (bd, J=13.8 Hz, 2H), 3.1–3.3 (m, 5H), 3.59 (t, J=6.4 Hz, 2H), 3.98 (bd, J=11z., 2H), 4.39 (t, J=5.9 Hz, 2H), 6.87 (s, 1H), 7.14 (m, 3H), 7.27 (d, J=3.9 Hz, 1H), 8.08 (bs, 1H), 8.73 (bs, 1H), 8.90 (bs, 1H), 9.21 (s, 1H).

EXAMPLE 28

1-(2-(3-Indolyl)ethyl)-4-(5-(benzodioxan-6-yl)pyrazol-3-yl)piperdine

In a manner similar to that described for EXAMPLE 1 but substituting 3-(2-bromoethyl)indole for 1-(2-bromoethyl)naphthalene in Step C, 1-(2-(3-indolyl)ethyl)-4-(5-(benzodioxan-6-yl)pyrazol-3-yl)piperdine was prepared, mp: 213°–214° C.

$^1$H NMR (CDCl$_3$): d 1.83 (m, 2H); 2.02 (d, J=10.7 Hz, 2H); 2.16 (t, J=11.3 Hz, 2H); 2.71 (m, 3H); 2.98 (m, 2H); 3.14 (d, J=8.5 Hz, 2H); 4.28 (s, 4H); 6.28 (s, 1H); 6.86 (d, J=8.2 Hz, 1H); 7.05 (m, 5H); 7.36 (d, J=8.3, 1H); 7.61 (d, J=7.7 Hz, 1H); 8.62 (br s, 1H).

EXAMPLE 29

1-(2-(3-Benzofuryl)ethyl)-4-(5-(benzodioxan-6-yl)pyrazol-3-yl)piperdine

In a manner similar to that described for EXAMPLE 1 but substituting 3-(2-bromoethyl)benzofuran for 1-(2-bromoethyl)naphthalene in Step C, 1-(2-(3-benzofuryl)ethyl)-4-(5-(benzodioxan-6-yl)pyrazol-3-yl)piperdine was prepared, mp: 183°–185° C.

$^1$H NMR (CDCl$_3$): d 1.85 (m, 2H); 2.02 (br d, J=11.9 Hz, 2H); 2.18 (br t, J=10.8 Hz, 2H); 2.72 (m, 3H); 2.90 (br t, J=7.7 Hz, 2H); 3.12 (br d, J=12.1 Hz, 2H); 4.27 (s, 4H); 6.28 (s, 1H); 6.88 (d, J=8.2 Hz, 1H); 7.22 (m, 4H); 7.45 (m, 2H); 7.56 (d, J=7.7 Hz, 1H); 9.7 (br s, 1H).

EXAMPLE 30

1-(Tetralin-2-yl)-4-[5-(pyridin-3-yl)[pyrazol-3-yl]piperdine

Step A: Ethyl 1-(tetralin-2-yl)piperdine-4-carboxylate

A solution of β-tetralone (11 g, 0.075 mol), ethyl isonipecotate (13 g, 0.083 mol) and p-toluene sulfonic add monohydrate (150 mg) in toluene (350 ml) under N$_2$ was heated to reflux with a Dean-Stark trap. After the theoretical amount of water (1.4 ml) was collected, the reaction mixture was poured into a saturated solution of NaHCO$_3$, separated and the aqueous layer further extracted with EtOAc (2×). The combined organic extracts were dried, filtered and concentrated to dryness to yield the corresponding enamine. The enamine (21.7 g) in THF (300 ml) was treated with AcOH (13.4 g, 0.22 mol) and sodium triacetoxy borohydride (17.4 g, 0.082 mol). The mixture was stirred and heated to 45° C. for 12 h. The reaction was then poured into a saturated solution of NaHCO$_3$ and the aqueous extracted with EtOAc (3×). The organic extracts were dried, filtered and concentrated to dryness to yield ethyl 1-(tetralin-2yl)piperdine-4-carboxylate.

Step B: 1-(Tetralin-2-yl)piperdine-4-carboxylic acid hydrochloride salt

Ethyl-1-(tetralin-2-yl)piperdine-4-carboxylate (7.1 g, 0.025 mol) was treated with 6N HCl (80 ml) at room temperature. After stirring overnight, the suspension was filtered off and the solid dried in vacuo to yield 1-(tetralin-2-yl)piperdine-4-carboxylic acid hydrochloride salt.

| Compound analyzed for C$_{16}$H$_{21}$NO$_2$.HCl.0.3H$_2$O. | | | | |
|---|---|---|---|---|
| Calc'd | C | 63.79 | Obs. | 63.87 |
|  | H | 7.56 |  | 7.33 |
|  | N | 9.65 |  | 4.77 |

Step C: 1-(Tetralin-2-yl)-4-(1-(3-hydroxy-1-oxo-3-(3-pyridinyl)-2-propenyl)piperdine A solution of 1-(tetralin-2-yl)piperdine-4-carboxylic acid hydrochloride (0.59 g, 0.002 mol) in H$_2$O (20 ml) was treated with NaHCO$_3$ (0.17 g, 0.002 mol). The solution was then concentrated to dryness and the solid residue was extracted several times with CHCl$_3$. The organic extracts were dried, filtered and concentrated to dryness to yield the acid.

The acid (0.52 g, 0.002 mol) in THF (10 ml) was treated under N$_2$ at room temperature with 1,1'-carbonyldiimidazole (0.34 g, 0.0021 ml) and the solution stirred for 45 min.

To a separate flask was added 3-acetylpyridine (0.27 g, 0.0021 mol) in THF (10 ml) and the solution cooled under N$_2$ to −78° C. To this solution was added dropwise via syringe at −78° C. lithium diisopropylamide (1.1 ml of a 2M solution in heptane-THF-ethylbenzene, 0.0022 mol). After aging for 5 min., the imidazolide solution was added dropwise at −78° C. The resulting thick suspension was then allowed to stir to room temperature. After 2 h, the clear yellow solution was poured into saturated NaHCO$_3$ solution and the aqueous layer was extracted with EtOAc (3×). The organic extracts were dried, filtered and concentrated to dryness. The crude residue was chromatographed on a Still column (40 mm) and the product eluted with 10% IPA/CHCl$_3$ saturated with NH$_3$ to yield 1-(tetralin-2-yl)-4-(1-(3-hydroxy-1-oxo-3-(3-pyridinyl)-2-propenyl)piperdine.

Step D:

In a manner similar to that described for EXAMPLE 1, but substituting 1-(tetralin-2-yl)-4-(1-(3-hydroxy-1-oxo-3-(3-pyridyl)-2-propenyl)piperdine for 1-(2-(1-naphthyl)ethyl)-4-(1-(3-hydroxy-1-oxo-3-(3-pyridinyl)-2-propenyl)piperdine in Step D, the free base of the "title" compound was obtained. The trihydrochloride hemihydrate was prepared from EtOH-HCl and crystallized from EtOH to yield 1-(tetralin-2-yl)-4-[5-(pyridin-3-yl)[pyrazol-3-yl]piperdine; mp 263°–5°.

| Compound analyzed for C$_{23}$H$_{25}$N$_4$.3HCl.0.5H$_2$O. | | | | |
|---|---|---|---|---|
| Calc'd | C | 6.14 | Obs. | 6.20 |
|  | H | 11.77 |  | 11.59 |
|  | N | 58.05 |  | 57.91 |

The $^1$H NMR of the free base (CDCl$_3$): d 1.65 (m, 1H),; 2.00 (m, 5H); 2.40 (m, 2H); 2.90 (m, 6H); 3.10 (bt, 2H); 6.4 (s, 1H); 7.1 (bs, 4H); 7.30 (dd, 1H); 8.05 (d, 1H); 8.55 (d, 1H); 9.00 (s, 1H).

EXAMPLES 31 & 32

1-(2-(1-Naphthyl)ethyl)-4-(3-(1,4-benzodioxan-6-yl)isoxazol-5-yl)piperdine and 1-(2-(1-Naphthyl)ethyl)-4-(5-(1,4-benzodioxan-6-yl)isoxazol-3-yl)piperdine

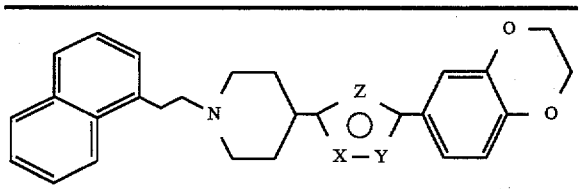

| | X | Y | Z |
|---|---|---|---|
| Example 31 | O | N | CH |
| Example 32 | N | O | CH |

In a manner similar to that described for EXAMPLE 1 but substituting 1,4-benzodioxan-6-yl methyl ketone for 3-acetylpyridine in Step A, 1-(1,1-dimethylethoxycarbonyl)-4-(1-(3-hydroxy-1-oxo-3-(1,4-benzodioxan-6-yl)-2-propenyl)piperdine was prepared.

Step B: 1-(1,1-dimethylethoxycarbonyl)-4-(3-(1,4-benzodioxan-6-yl)-3-hydroxy-3,4-dihydroisoxazol-5-yl)piperdine and 1-(1,1-dimethylethoxy-carbonyl)-4-(5-(1,4-benzodioxan-6-yl)-3-hydroxy-3,4-dihydroisoxazol-3-yl)piperdine.

Hydroxylamine hydrochloride (69.49 mg, 2.05 mmol) was added to 1-(1,1-dimethylethoxycarbonyl)-4-(1-(3-hydroxy-1-oxo-3-(1,4-benzodioxan-6-yl)-2-propenyl)piperdine (400 mg, 1.03 mmol) and diisopropylamine (357 ml, 2.05 mmol) dissolved in methanol (5 ml) and dimethylformamide (2 ml). A second portion of hydroxylamine hydrochloride (143 mg) was added after heating for 6 h at 50° C. and the reaction mixture was stirred for 16 h at 50° C. Water (25 ml) was added, the mixture extracted with ethyl acetate (3×35 ml) and the combined organic layers washed with water and brine, dried over $Na_2SO_4$, and evaporated in vacuo to afford the crude oil residue which contained a mixture of 1-(1,1-dimethylethoxycarbonyl)-4-(3-(1,4-benzodioxan-6-yl)-3-hydroxy-3,4-dihydroisoxazol-5-yl)piperdine and 1-(1,1-dimethylethoxy-carbonyl)-4-(5-(1,4-benzodioxan-6-yl)-3-hydroxy-3,4-dihydroisoxazol-3-yl)piperdine.

Without purification, the 3-hydroxy-3,4-dihydroisoxazole mixture was dissolved in methylene chloride (25 ml), cooled to 0° C. under argon, and treated with mesyl chloride (110 mg, 74.4 ml, 0.961 mmol) and triethylamine (124 mg, 167 ml, 0.961 mmol). After warming to room temperature, dehydration to the desired isoxazole mixture of 1-(1,1-dimethylethoxycarbonyl)-4-(3-(1,4-benzodioxan-6-yl)isoxazol-5-yl)piperdine and 1-(1,1-dimethylethoxy-carbonyl)-4-(5-(1,4-benzodioxan-6-yl)isoxazol-3-yl)piperdine was effected by warming to 50° C. in an oil bath for 3 hours. Workup afforded an oil residue following rotavaporation, partitioning between ethyl acetate/sodium bicarbonate, washing EtOAc with brine, drying over $Na_2SO_4$, filtration and rotavaporation.

Step C: 4-(3-(1,4-benzodioxan-6-yl)isoxazol-5-yl)piperdine and 1-(1,1-dimethylethoxy-carbonyl)-4-(5-(1,4-benzodioxan-6-yl)isoxazol-3-yl)piperdine To a 100 mL round bottomed flask with a stirring bar and a sparging tube was added 1-(1,1-dimethylethoxycarbonyl)-4-(3-(1,4-benzodioxan-6-yl)isoxazol-5-yl)piperdine and 1-(1,1-dimethylethoxy-carbonyl)-4-(5-(1,4-benzodioxan-6-yl)isoxazol-3-yl)piperdine (350 mg, 0.83 mmol) and dry EtOAc (35 mL). This solution was cooled in an ice bath and dry HCl gas was bubbled through the mixture vigorously for 5 min. The mixture was stirred an additional 30 min. at 0° C. then the excess HCl was removed with argon gas. The solvent was removed in vacuo and the hydrochloride salt was converted to freebase using 1:1 aqueous saturated sodium carbonate:brine, extracted with EtOAc (3×35 ml), washed with brine, dried over $Na_2SO_4$, filtered and rotavaped to afford a mixture of 4-(3-(1,4-benzodioxan-6-yl)isoxazol-5-yl)piperdine and 1-(1,1-dimethylethoxy-carbonyl)-4-(5-(1,4-benzodioxan-6-yl)isoxazol-3-yl) piperdine as an oil residue.

Step D: 1-(2-(1-Naphthyl)ethyl)-4-(3-(1,4-benzodioxan-6-yl)isoxazol-5-yl)piperdine and 1-(2-(1-Naphthyl)ethyl)-4-(5-(1,4-benzodioxan-6-yl)isoxazol-3-yl)piperdine To 25 mL round bottomed flask with a stirring bar and an argon inlet was added 4-(3-(1,4-benzodioxan-6-yl)isoxazol-5-yl)piperdine and 1-(1,1-dimethylethoxy-carbonyl)-4-(5-(1,4-benzodioxan-6-yl)isoxazol-3-yl)piperdine (231 mg, 0.809 mmol), 1-naphthylacetaldehyde (165.3 mg, 0.971 mmol) 1,2-dichloroethane (5 mL), glacial acetic acid (55.6 ml, 0.971 mmol) and sodium triacetoxyborohydride (411.6 mg 1.942 mmol). This mixture was stirred at room temperature for 24 h then quenched with saturated aqueous sodium bicarbonate (75 ml), extracted with EtOAc (3×75 ml) washed with brine, dried ($Na_2SO_4$) and filtered. Removal of the solvent in vacuo gave a tan oil. This material was chromatographed on silica gel using 3% 2-propanol in $NH_3$ saturated $CHCl_3$ as eluant. The major regioisomer was obtained as an oil (upper $R_f$) which was crystallized from EtOAc as the hydrochloride salt, 1-(2-(1-naphthyl)ethyl)-4-(3-(1,4-benzodioxan-6-yl)isoxazol-5-yl)piperdine hydrochloride, mp 239.5°–241° C. FAB MS data are consistent with theoretical m/e=441. $^1$H NMR free base ($CDCl_3$): d 1.90 (m, 2H); 2.13 (br d, J=11.5 Hz, 2H); 2.25 (br t, J=9.5 Hz, 2H); 2.78 (m, 1H), 3.16 (br d, J=11.6 Hz, 2H); 3.31 (m, 2H); 4.28 (s, 4H); 6.46 (s, 1H); 6.92 (d, J=8.2 Hz, 1H); 7.25–7.54 (m, 7H); 7.73 (d, J=8.1 Hz, 1H); 7.86 (dd, J=1.5, 8.3 Hz, 1H); 8.07 (d, J=8.4 Hz, 1H).

The minor isoxazole regioisomer (lower $R_f$) required preparative HPLC purification to afford 1-(2-(1-naphthyl)ethyl)-4-(5-(1,4-benzodioxan-6-yl)isoxazol-3-yl)piperdine trifluoroacetate salt after freeze-drying from dioxane. FAB MS data and $^1$H NMR data (TFA salt, $CD_3OD$) are consistent with the proposed structure.

EXAMPLE 33

As a specific embodiment of an oral composition, 100 mg of the compound of Example 1 is formulated with sufficient finely divided lactose to provide a total amount of 580 to 590 mg to fill a size O hard gel capsule.

EXAMPLE 34

Screening assay: Alpha 1a Adrenergic Receptor Binding

Membranes prepared from the stably transfected human α1a cell line (ATCC CRL 11140) were used to identify compounds that bind to the human alpha 1a adrenergic receptor. These competition binding reactions (total volume=200 ul) contained 50 mM Tris-HCl pH. 7.4, 5 mM EDTA, 150 mM NaCl, 100 pM [$^{125}$I]-HEAT, membranes prepared from the α1a cell line and increasing amounts of unlabeled ligand. Reactions were incubated at room temperature for one hour with shaking. Reactions were filtered onto Whatman GF/C glass fiber filters with a Inotec 96 well cell harvester. Filters were washed three times with ice cold buffer and bound radioactivity was determined (Ki). Representative compounds of the present invention were found to have Ki values ≦1 μM.

EXAMPLE 35

Selective Binding assays

Membranes prepared from stably transfected human a1d and α1b cell lines (ATCC CRL 11138 and CRL 11139, respectively) were used to identify compounds that selectively bind to the human alpha1a adrenergic receptor. These competition binding reactions (total volume=200 ul) contained 50 mM Tris-HCl pH. 7.4, 5 mM EDTA, 150 mM NaCl, 100 pM [$^{125}$I]-HEAT, membranes prepared from cell lines transfected with the respective alpha 1 subtype expression plasmid and increasing amounts of unlabeled ligand. Reactions were incubated at room temperature for one hour with shaking. Reactions were filtered onto Whatman GF/C glass fiber filters with a Inotec 96 well cell harvester. Filters were washed three times with ice cold buffer and bound radioactivity was determined CKi).

EXAMPLE 36

EXEMPLARY COUNTERSCREENS

1. Assay Title Dopamine D2, D4 in vitro screen
Objective of the Assay
The objective of this assay is to eliminate agents which specifically affect binding of [3H] spiperone to cells expressing human dopamine receptors D2, D3 or D4.
Method: Modified from VanTol et al (1991); *Nature (Vol 350)* Pg 610–613
Frozen pellets containing specific dopamine receptor subtypes stably expressed in clonal cell lines are lysed in 2 ml lysing buffer (10 mM Tris-HCl/5 mM Mg, pH 7.4). Pellets obtained after centrifuging these membranes (15' at 24,450 rpm) are resuspended in 50 mM Tris-HCl pH 7.4 containing EDTA, MgCl[2], KCl, NaCl, CaCl[2] and ascorbate to give a 1 Mg/mL suspension. The assay is initiated by adding 50–75 μg membranes in a total volume of 500 μl containing 0.2 nM [3H]-spiperone. Non-specific binding is defined using 10 μM apomorphine. The assay is terminated after a 2 hour incubation at room temperature by rapid filtration over GF/B filters presoaked in 0.3% PEI, using 50 mM Tris-HCl pH 7.4.
2. Assay Title Serotonin 5HT1a
Objective of the Assay
The objective of this assay is to eliminate agents which specifically affect binding to cloned human 5HT1a receptor.
Method: Modified from Schelegel and Peroutka *Biochemical Pharmacology* 35:1943–1949 (1986)
Mammalian cells expressing cloned human 5HT1a receptors are lysed in ice-cold 5 mM Tris-HCl, 2 mM EDTA (pH 7.4) and homogenized with a polytron homogenizer. The homogenate is centrifuged at 1000×g for 30', and then the supernatant is centrifuged again at 38,000×g for 30'. The binding assay contains 0.25 nM [3H]8-OH-DPAT (8-hydroxy-2-dipropylamino-1,2,3,4-tetrahydronaphthalene) in 50 mM Tris-HCl, 4 mM CaCl$_2$ and 1 mg/ml ascorbate. Non-specific binding is defined using 10 μM propranolol. The assay is terminated after a 1 hour incubation at room temperature by rapid filtration over GF/Cfilters.

EXAMPLE 37

EXEMPLARY FUNCTIONAL ASSAYS

In order to confirm the specificity of compounds for the human alpha1a adrenergic receptor and to define the biological activity of the compounds, the following functional tests may be performed:
1. In vitro Rat, Dog and Human Prostate and Dog Urethra
Taconic Farms Sprague-Dawley male rats, weighing 250–400 grams are sacrificed by cervical dislocation under anesthesia (methohexital; 50 mg/kg, i.p.). An incision is made into the lower abdomen to remove the ventral lobes of the prostate. Each prostate removed from a mongrel dog is cut into 6–8 pieces longitudinally along the urethra opening and stored in ice-cold oxygenated Krebs solution overnight before use if necessary. Dog urethra proximal to prostate is cut into approximately 5 mm rings, the rings are then cut open for contractile measurement of circular muscles. Human prostate chips from transurethral surgery of benign prostate hyperplasia are also stored overnight in ice-cold Krebs solution if needed.
The tissue is placed in a Petri dish containing oxygenated Krebs solution [NaCl, 118 mM; KCl, 4.7 mM; CaCl$_2$, 2.5 mM; KH$_2$PO$_4$, 1.2 mM; MgSO$_4$, 1.2 mM; NaHCO$_3$, 2.0 mM; dextrose, 11 mM] warmed to 37° C. Excess lipid material and connective tissue are carefully removed. Tissue segments are attached to glass tissue holders with 4-0 surgical silk and placed in a 5 ml jacketed tissue bath containing Krebs buffer at 37° C., bubbled with 5% CO$_2$/95% O$_2$. The tissues are connected to a Statham-Gould force transducer; 1 gram (rat, human) or 1.5 gram (dog) of tension is applied and the tissues are allowed to equilibrate for one hour. Contractions are recorded on a Hewlett-Packard 7700 series strip chart recorder.
After a single priming dose of 3 μM (for rat), 10 μM (for dog) and 20 μM (for human) of phenylephrine, a cumulative concentration response curve to an agonist is generated; the tissues are washed every 10 minutes for one hour. Vehicle or antagonist is added to the bath and allowed to incubate for one hour, then another cumulative concentration response curve to the agonist is generated.
EC$_{50}$ values are calculated for each group using GraphPad Inplot software. pA$_2$ (−log K$_b$) values were obtained from Schild plot when three or more concentrations were tested. When less than three concentrations of antagonist are tested, Kb values are calculated according to the following formula $$K_b=[B]/x-1$$

where x is the ratio of EC$_{50}$ of agonist in the presence and absence of antagonist and [B] is the antagonist concentration.
2. Measurement of Intra-Urethral Pressure in Anesthetized Dogs
PURPOSE: Benign prostatic hyperplasia causes a decreased urine flow rate that may be produced by both passive physical obstruction of the prostatic urethra from increased prostate mass as well as active obstruction due to prostatic contraction. Alpha adrenergic receptor antagonists such as prazosin and terazosin prevent active prostatic contraction, thus improve urine flow rate and provide symptomatic relief in man. However, these are non-selective alpha-1 receptor antagonists which also have pronounced vascular effects. Because we have identified the alpha-1a receptor subtype as the predominent subtype in the human prostate, it is now possible to specifically target this receptor to inhibit prostatic contraction without concomitant changes in the vasculature. The following model is used to measure adrenergically mediated changes in intra-urethral pressure and arterial pressure in anesthetized dogs in order to evaluate the efficacy and potency of selective alpha adrenergic receptor antagonists. The goals are to: 1) identify the alpha-1 receptor subtypes responsible for prostatic/urethral contraction and vascular responses, and 2) use this model to evaluate novel selective alpha adrenergic antagonists. Novel and standard alpha adrenergic antagonists may be evaluated in this manner.

METHODS: Male mongrel dogs (7–12 kg) are used in this study. The dogs are anesthetized with pentobarbital sodium (35 mg/kg, i.v. plus 4 mg/kg/hr iv infusion). An endotracheal tube is inserted and the animal ventilated with room air using a Harvard instruments positive displacement large animal ventilator. Catheters (PE 240 or 260) are placed in the aorta via the femoral artery and vena cava via the femoral veins (2 catheters, one in each vein) for the measurement of arterial pressure and the administration of drugs, respectively. A supra-pubic incision ~½ inch lateral to the penis is made to expose the urethers, bladder and urethra. The urethers are ligated and cannulated so that urine flows freely into beakers. The dome of the bladder is retracted to facilitate dissection of the proximal and distal urethra. Umbilical tape is passed beneath the urethra at the bladder neck and another piece of umbilical tape is placed under the distal urethra approximately 1–2 cm distal to the prostate. The bladder is incised and a Millar micro-tip pressure transducer is advanced into the urethra. The bladder incision is sutured with 2-0 or 3-0 silk (purse-string suture) to hold the transducer. The tip of the transducer is placed in the prostatic urethra and the position of the Millar catheter is verified by gently squeezing the prostate and noting the large change in urethral pressure.

Phenylephrine, an alpha-1adrenergic agonist, is administered (0.1–100 ug/kg, iv; 0.05 ml/kg volume) in order to construct dose response curves for changes in intra-urethral and arterial pressure. Following administration of increasing doses of an alpha adrenergic antagonist (or vehicle), the effects of phenylephrine on arterial pressure and intra-urethral pressure are re-evaluated. Four or five phenylephrine dose-response curves are generated in each animal (one control, three or four doses of antagonist or vehicle). The relative antagonist potency on phenylephrine induced changes in arterial and intra-urethral pressure are determined by Schild analysis. The family of averaged curves are fit simultaneously (using ALLFIT software package) with a four parameter logistic equation constraining the slope, minimum response, and maximum response to be constant among curves. The dose ratios for the antagonist doses (rightward shift in the dose-response curves from control) are calculated as the ratio of the $ED_{50}$'s for the respective curves. These dose-ratios are then used to construct a Schild plot and the Kb (expressed as ug/kg, iv) determined. The Kb (dose of antagonist causing a 2-fold rightward shift of the phenylephrine dose-response curve) is used to compare the relative potency of the antagonists on inhibiting phenylephrine responses for intra-urethral and arterial pressure. The relative selectivity is calculated as the ratio of arterial pressure and intra-urethral pressure Kb's. Effects of the alpha-I antagonists on baseline arterial pressure are also monitored. Comparison of the relative antagonist potency on changes in arterial pressure and intra-urethral pressure provide insight as to whether the alpha receptor subtype responsible for increasing intra-urethral pressure is also present in the systemic vasculature. According to this method, one is able to confirm the selectivity of alpha1a adrenergic receptor antagonists that prevent the increase in intra-urethral pressure to phenylephrine without any activity at the vasculature.

While the foregoing specification teaches the principles of the present invention, with examples provided for the purpose of illustration, it will be understood that the practice of the invention encompasses all of the usual variations, adaptations and/or modifications as come within the scope of the following claims and their equivalents.

What is claimed is:

1. A method of treating benign prostatic hypertrophy in a subject in need thereof which comprises administering to the subject a therapeutically effective amount of a compound of formula I

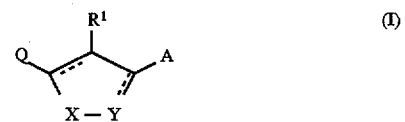

wherein the broken lines represent two non-adjacent double bonds in any position within the five-membered ring;

one of X and Y represents nitrogen, and the other of X and Y represents oxygen, sulphur or N—$R^2$;

Q represents a substituted five- or six-membered monocyclic heteroaliphatic ring selected from Qa to Qe

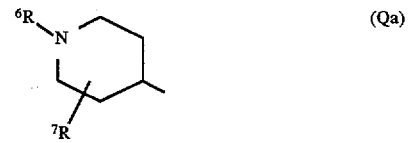

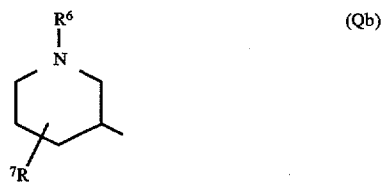

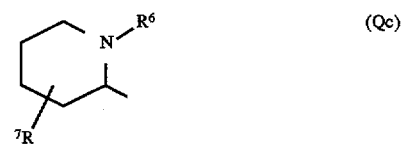

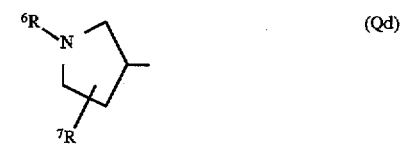

and is linked to the five-membered heteroatomic ring containing the moieties X and Y via a carbon atom;

wherein $R^6$ is $C_{0-6}$ alkyl substituted with a monocyclic or polycyclic aromatic or heteroaromatic group selected from:

phenyl; 1-naphthyl; 2-naphthyl; benzothiophene; benzofuran; indole; quinoline; isoquinoline; indazole; benzisoxazole; benzimidazol(on)e; thiophene; furan; or pyridine; each of which may or may not be substituted with one or more of $C_{1-6}$ alkyl; $C_{1-6}$ alkoxy($C_{1-6}$)alkyl; $C_{1-6}$ alkoxy; cyano; nitro; carboxamido; amidino; amino; halogen; sulfonamido; amidosulfonyl; or hydroxy;

$R^7$ represents hydrogen, hydrocarbon, an ether or a heterocyclic group;

$R^1$ represents hydrogen, halogen, $C_{1-6}$ alkyl, hydroxy or $C_{1-6}$ alkoxy;

$R^2$ represents hydrogen or $C_{1-6}$ alkyl;

A represents a group of formula (iv):

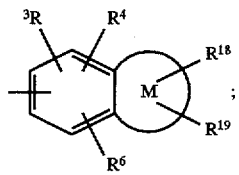
(iv)

$R^3$, $R^4$ and $R^5$ are each independently selected from hydrogen, hydrocarbon, a heterocyclic group, halogen, cyano trifluoromethyl, nitro, —$OR^a$, —$SR^a$, —$SOR^a$, —$SO_2R^a$, —$SO_2NR^aR^b$, —$NR^aR^b$, —$NR^aCOR^b$, —$NR^aCO_2R^b$, —$COR^a$, —$CO_2R^a$ or —$CO_2NR^aR^b$;

$R^a$ and $R^b$ independently represent hydrogen, hydrocarbon or a heterocyclic group;

the ring M is optionally an additional ring or ring system such that the entire structure (iv) is dicyclic, or polycyclic aromatic or heteroaromatic ring system, selected from: benzodioxane; methylenedioxyphenyl; indane; 2,3-dihydrobenzofuran; 2,7-dihydroizobenzofuran; 1-naphthyl; 2-naphthyl; benzothiophene; benzofuran; indole; quinoline; isoquinoline; indazole; benzisoxazole; benzthiazole; or benzimidazol(on)e; each of which may be substituted with $R^3$, $R^4$ and $R^5$, as described above and, in addition, with $R^{18}$, and $R^{19}$, each of which may be independently:

$C_{1-6}$ alkyl; $C_{1-6}$ alkoxy-$C_{1-6}$ alkyl; $C_{1-6}$ alkoxy; cyano; nitro; carboxamido; amidino; amino; halo; sulfonamido; amidosulfonyl; hydrogen or hydroxy;

the heterocyclic group, at each occurrence, is independently selected from azetidinyl, pyrrolidyl, piperidyl, pyridyl, quinolyl, isoquinolyl, pyranyl, furyl, benzofuryl, dibenzofuryl, thienyl, benzothienyl, indolyl, imidazolyl, oxadiazolyl, thiadiazolyl, azetidinyl($C_{1-6}$)alkyl, pyrrolidyl($C_{1-6}$)alkyl, piperidyl ($C_{1-6}$)alkyl, pyridyl($C_{1-6}$)alkyl, quinolyl($C_{1-6}$)alkyl, isoquinolyl($C_{1-6}$)alkyl, pyranyl($C_{1-6}$)alkyl, furyl($C_{1-6}$) alkyl, benzofuryl($C_{1-6}$)alkyl, dibenzofuryl($C_{1-6}$)alkyl, thienyl($C_{1-6}$)alkyl, benzothienyl($C_{1-6}$)alkyl, indolyl ($C_{1-6}$)alkyl, imidazolyl($C_{1-6}$)alkyl, oxadiazolyl($C_{1-6}$) alkyl, or thiadiazolyl($C_{1-6}$)alkyl;

and the pharmaceutically acceptable salts thereof.

2. The method of claim 1 wherein the five-membered heteroaromatic ring containing the moieties X and Y represented by formula I is a substituted isoxazole, isothiazole or pyrazole ring.

3. The method of claim 1 wherein the compound is represented by the formula:

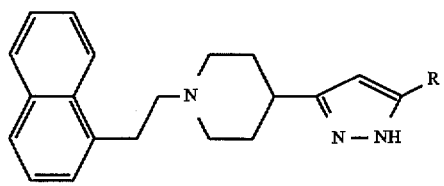

wherein R is selected from 2-naphthyl; 6-benzodioxane; 3,4-methylenedioxyphenyl; or 6-quinolinyl.

4. The method of claim 1, wherein the compound additionally does not cause a fall in blood pressure at dosages effective to alleviate benign prostatic hypertophy.

5. The method of claim 1 wherein the compound is selected from:

1-(2-(1-Naphthyl)ethyl)-4-(5-(2-naphthyl)pyrazol-3-yl) piperdine;

1-(2-(1-Naphthyl)ethyl)-4-(5-(benzoioxan-6-yl)pyrazol-3-yl)piperdine;

1-(2-(1-Naphthyl)ethyl)-4-(5-(3,4-methylenedioxyphenyl) pyrazol-3-yl)piperdine;

1-(2-(1-Naphthyl)ethyl)-4-(5-(6-quino linyl)pyrazol-3-yl) piperidine;

1-(2-(3-Indolyl)ethyl)-4-(5-(benzodioxan-6-yl)pyrazol-3-yl)piperdine;

1-(2-(3-Benzofuryl)ethyl)-4-(5-(benzodioxan-6-yl)pyrazol-3-yl)piperdine;

1-(2-(1-Naphthyl)ethyl)-4-(3-(1,4-benzodioxan-6-yl) isoxazol-5-yl)piperdine; and 1-(2-(1-Naphthyl)ethyl)-4-(5-(1,4-benzodioxan-6-yl) isoxazol-3-yl)piperdine;

and the pharmaceutically acceptable salts thereof.

6. A compound represented by formula I

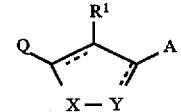
(I)

wherein the broken lines represent two non-adjacent double bonds in any position within the five-membered ring;

one of X and Y represents nitrogen, and the other of X and Y represents oxygen, sulphur or N—$R^2$;

Q represents a substituted five- or six-membered monocyclic heteroaliphatic ring selected from Qa to Qe

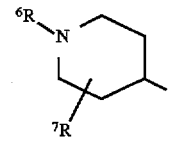
(Qa)

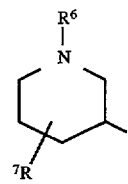
(Qb)

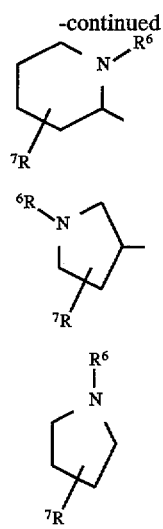

and is linked to the five-membered heteroatomic ring containing the moieties X and Y via a carbon atom; wherein $R^6$ is $C_{0-6}$ alkyl substituted with a monocyclic or polycyclic aromatic or heteroaromatic group selected from: phenyl; 1-naphthyl; 2-naphthyl; benzothiophene; benzofuran; indole; quinoline; isoquinoline; indazole; benzisoxazole; benzimidazol(on)e; thiophene; furan or pyridine; each of which may or may not be substituted with one or more of $C_{1-6}$ alkyl; $C_{1-6}$ alkoxy($C_{1-6}$)alkyl; $C_{1-6}$ alkoxy; cyano; nitro; carboxamido; amidino; amino; halogen; sulfonamido; amidosulfonyl; or hydroxy;

$R^7$ represents hydrogen, hydrocarbon, an ether or a heterocyclic group;

$R^1$ is selected from hydrogen, halogen, $C_{1-6}$ alkyl, hydroxy or $C_{1-6}$ alkoxy;

$R^2$ is selected from hydrogen or $C_{1-6}$ alkyl; and

A represents a group of formula (iv):

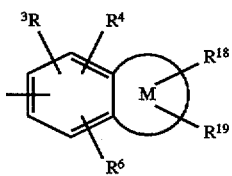

in which $R^3$, $R^4$ and $R^5$ are each independently selected from hydrogen, hydrocarbon, a heterocyclic group, halogen, cyano, trifluoromethyl, nitro, —$OR^a$, —$SR^a$, —$SOR^a$, —$SO_2R^a$, —$SO_2NR^aR^b$, —$NR^aR^b$, —$NR^aCOR^b$, —$NR^aCO_2R^b$, —$COR^a$, —$CO_2R^a$ or —$CO_2NR^aR^b$;

$R^a$ and $R^b$ are each independently selected from hydrogen, hydrocarbon or a heterocyclic group;

the ring M is optionally an additional ring or ring system such that the entire structure (iv) is a dicyclic, or polycyclic aromatic or heteroaromatic ring system, selected from: benzodioxane; dioxane; methylenedioxyphenyl; indane; 2,3-dihydrobenzofuran; 2,7-dihydroizobenzofuran; 1-naphthyl; 2-naphthyl; benzothiophene; benzofuran; indole; quinoline; isoquinoline; indazole; benzisoxazole; benzthiazole; or benzimidazol(on)e; each of which may be substituted with $R^3$, $R^4$ and $R^5$, as described above and, in addition, with $R^{18}$, and $R^{19}$, each of which may be independently: $C_{1-6}$ alkyl; $C_{1-6}$ alkoxy ($C_{1-6}$)alkyl; $C_{1-6}$ alkoxy; cyano; nitro; carboxamido; amidino; amino; halo; sulfonamido; amidosulfonyl; hydrogen or hydroxy;

the heterocyclic group, at each occurrence, is independently selected from azetidinyl, pyrrolidyl, piperidyl, pyridyl, quinolyl, isoquinolyl, pyranyl, furyl, benzofuryl, dibenzofuryl, thienyl, benzothienyl, indolyl, imidazolyl, oxadiazolyl, thiadiazolyl, azetidinyl($C_{1-6}$)alkyl, pyrrolidyl($C_{1-6}$)alkyl, piperidyl ($C_{1-6}$)alkyl, pyridyl($C_{1-6}$)alkyl, quinolyl($C_{1-6}$)alkyl, isoquinolyl($C_{1-6}$)alkyl, pyranyl($C_{1-6}$)alkyl, furyl($C_{1-6}$) alkyl, benzofuryl($C_{1-6}$)alkyl, dibenzofuryl($C_{1-6}$)alkyl, thienyl($C_{1-6}$)alkyl, benzothienyl($C_{1-6}$)alkyl, indolyl ($C_{1-6}$)alkyl, imidazolyl($C_{1-6}$)alkyl, oxadiazolyl($C_{1-6}$) alkyl, or thiadiazolyl($C_{1-6}$)alkyl;

and the pharmaceutically acceptable salts thereof.

7. A pharmaceutical composition comprising a pharmaceutically acceptable carrier and a therapeutically effective amount of the compound as claimed in claim 6.

8. A method of inhibiting contraction of prostate tissue in a subject in need thereof which comprises administering to the subject a therapeutically effective amount of the compound of claim 1.

9. The method of inhibiting contraction of prostate tissue of claim 8, wherein the compound additionally does not cause a fall in blood pressure at dosages effective to inhibit contraction of prostate tissue.

10. A method of treating a disease which is susceptible to treatment by antagonism of the alpha 1a receptor which comprises administering to a subject in need thereof of amount of the compound of claim 1 effective to treat the disease.

11. A compound selected from:
1-(2-(1—Naphthyl)ethyl)-4-(5-(benzodioxan-6-yl)pyrazol-3-yl)piperdine;
1-(2-(1—Naphthyl)ethyl)-4-(5-(3,4-methylenedioxyphenyl)pyrazol-3-yl)-piperdine;
1-(2-(1—Naphthyl)ethyl)-4-(5-(6-quinolinyl)pyrazol-3-yl)piperdine;
1-(2-(3-Indolyl)ethyl)-4-(5-(benzodioxan-6-yl)pyrazol-3-yl)piperdine;
1-(2-(3-Benzofuryl)ethyl)-4-(5-(benzodioxan-6-yl)pyrazol-3-yl)piperdine;
1-(2-(1—Naphthyl)ethyl)-4-(3-(1,4-benzodioxan-6-yl)isoxazol-5-yl)piperdine; and
1-(2-(1—Naphthyl)ethyl)-4-(5-(1,4-benzodioxan-6-yl)isoxazol-3-yl)piperdine;

and the pharmaceutically acceptable salts thereof.

12. The method of claim 10 wherein the compound is selected from:
1-(2-(1—Naphthyl)ethyl)-4-(5-(2-naphthyl)pyrazol-3-yl)piperdine;
1-(2-(1—Naphthyl)ethyl)-4-(5-(benzodioxan-6-yl)pyrazol-3-yl)piperdine;
1-(2-(1—Naphthyl)ethyl)-4-(5-(3,4-methylenedioxyphenyl)pyrazol-3-yl)piperdine;
1-(2-(1—Naphthyl)ethyl)-4-(5-(6-quinolinyl)pyrazol-3-yl)piperdine;
1-(2-(3-Indolyl)ethyl)-4-(5-(benzodioxan-6-yl)pyrazol-3-yl)piperdine; and
1-(2-(3-Benzofuryl)ethyl)-4-(5-(benzodioxan-6-yl)pyrazol-3-yl)piperdine;

and the pharmaceutically acceptable salts thereof.

* * * * *